(54) ALPHA 1A ADRENERGIC RECEPTOR ANTAGONISTS

(75) Inventors: Daniel R. Sidler, Whitehouse Station; Robert D. Larsen, Bridgewater, both of NJ (US); Wenjie Li, Pittsburgh, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/563,203

(22) Filed: May 2, 2000

Related U.S. Application Data

(62) Division of application No. 09/122,301, filed on Jul. 24, 1998, now Pat. No. 6,207,444.
(60) Provisional application No. 60/054,815, filed on Aug. 5, 1997, and provisional application No. 60/054,902, filed on Aug. 5, 1997.

(51) Int. Cl.$^7$ .................................................. C07D 239/22
(52) U.S. Cl. .............................................................. 544/316
(58) Field of Search ............................................. 544/316

(56) References Cited

U.S. PATENT DOCUMENTS 5,786,472   7/1998   Hu et al. ............................... 544/318

FOREIGN PATENT DOCUMENTS

| WO 96/14846 | 5/1996 | (WO) . |
| WO 97/21687 | 6/1997 | (WO) . |
| WO 98/57632 | 12/1998 | (WO) . |
| WO 98/57638 | 12/1998 | (WO) . |
| WO 98/57639 | 12/1998 | (WO) . |
| WO 98/57640 | 12/1998 | (WO) . |
| WO 98/57641 | 12/1998 | (WO) . |
| WO 98/57642 | 12/1998 | (WO) . |
| WO 99/25345 | 5/1999 | (WO) . |

OTHER PUBLICATIONS

Atwal et al., "Dihydropyrimidine Calcium Channel Blockers. 2. 3–Substituted–4–aryl–1,4–dihydro–6–methyl–5–pyrimidinecarboxylic Acid Esters as Potent Mimics of Dihydropyridines", J. Med. Chem., vol. 33, pp. 2629–2635 (1990).

Kappe et al., "Synthesis and Reactions of Biginelli Compounds. 5. Facile Preparation and Resolution of a Stable 5–Dihydropyrimidinecarboxylic Acid", Tetrahedron, vol. 48, No. 26, pp. 5473–5480, (1992).

Atwal et al.., "Dihydropyrimidine Calcium Channel Blockers. 3. 3–Carbamoyl–4–aryl–1,2,3,4–tetrahydro–6–methyl–5–pyrimidinecarboxylic Acid Esters as Oraly Effective Antihypertensive Agents", J. Med. Chem., vol. 34, pp. 806–811, (1991).

Kumar et al., "Design, Synthesis and Biological Evaluation of 1,3–Diaminopropanes: A New Class of Polyamine Analogs as Leishmanicidal Agents", Bio. & Med. Chemistry Letters, vol. 7, No. 6, pp. 675–680 (1997).

*Primary Examiner*—Richard L. Raymond
(74) *Attorney, Agent, or Firm*—Baerbel R. Brown; Kenneth R. Walton; Melvin Winokur

(57) ABSTRACT

This invention relates to crystalline pharmaceutically acceptable salts of an alpha 1a adrenergic receptor antagonist, Compound A, which are useful in the treatment of benign prostatic hyperplasia. Pharmaceutical compositions employing the crystalline salts, and processes for making and using the crystalline salts and pharmaceutical compositions of Compound A are also disclosed. This invention further relates to a process for obtaining enantiomerically pure intermediate useful for the synthesis of end product alpha 1a adrenergic receptor antagonists. The end product compounds are useful for the treatment of benign prostatic hyperplasia and for relaxing lower urinary tract tissue. The invention also relates to a process for preparing a class of dihydropyrimidinone compounds of which Compound A is a member, wherein the process involves deprotonating a dihydropyrimidinone compound and then coupling the deprotonated derivative with a primary amine.

7 Claims, No Drawings

ALPHA 1A ADRENERGIC RECEPTOR ANTAGONISTS

This application is a division of U.S. Ser. No. 09/122,301, filed Jul. 24, 1998, now U.S. Pat. No. 6,207,444, the benefit of U.S. Provisional Application Ser. No. 60/054,815, filed Aug. 5, 1997 and U.S. Provisional Application Ser. No. 60/054,902, file Aug. 5, 1997.

FIELD OF THE INVENTION

The present invention provides pharmaceutically acceptable salts, and process for manufacture, of an alpha 1a adrenergic receptor antagonist. More specifically, the invention provides crystalline pharmaceutically acceptable salts (e.g., the tartrate salt) of the alpha 1a adrenergic receptor, Compound A, having substantially improved physical properties as compared to the previously known amorphous salts.

The present invention also provides an improved process for making an alpha 1a adrenergic receptor antagonist useful for treating benign prostatic hyperplasia. More specifically, the invention provides an enzymatic resolution of a dihydropyrimidinone methyl ester which is an intermediate in the preparation of the alpha 1a adrenergic receptor antagonist, Compound A.

The present invention further provides a chemical process for making a class of dihydropyrimidinone compounds of which Compound A is a member. The process involves deprotonating a dihydropyrimidinone and then coupling the deprotonated derivative with a primary amine.

BACKGROUND OF THE INVENTION

Benign prostatic hyperplasia, also known as benign prostatic hypertrophy or BPH, is an illness typically affecting men over fifty years of age, increasing in severity with increasing age. The symptoms of the condition include, but are not limited to, increased difficulty in urination and sexual dysfunction. These symptoms are induced by enlargement, or hyperplasia, of the prostate gland. As the prostate increases in size, it impinges on free-flow of fluids through the male urethra. Concomitantly, the increased noradrenergic innervation of the enlarged prostate leads to an increased adrenergic tone of the bladder neck and urethra, further restricting the flow of urine through the urethra.

Recently, a number of alpha 1a adrenergic receptor antagonist compounds have been disclosed as being useful in the treatment of BPH. These alpha 1a adrenergic receptor antagonists and their utility in treating BPH and inhibiting contraction of lower urinary tract tissue are described in PCT International Application Publication No. WO 96/14846, published May 23, 1996. More particularly, the compound (+)-5-Methoxycarbonyl-6-(3,4-difluorophenyl)-4-methoxymethyl-1-{N-[3-(4-(2-pyridyl)piperidin-1-yl)propyl]}-carboxamido-2-oxo-1,2,3,6-tetrahydropyrimidine, disclosed in Example 30 of WO 96/14846, and referred to herein as "Compound A," is a potent and selective antagonist of the alpha 1a adrenergic receptor antagonist and is useful in the treatment of BPH.

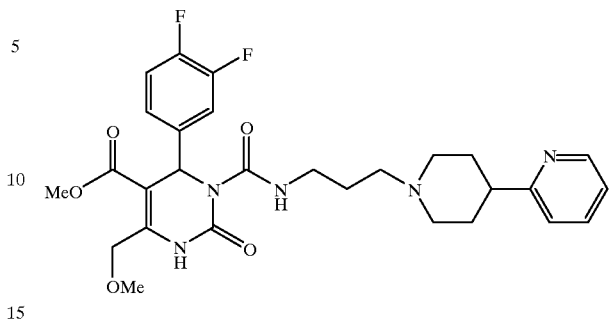

Compound A

Compound A is prepared according to the procedure of Example 30 in WO 96/14846 or according to the processes disclosed in detail herein. The identification of Compound A as an alpha 1a adrenergic receptor antagonist was established according to the assays described in WO 96/14846.

Preparation of an acceptable salt of Compound A suitable for pharmaceutical development proved problematic. Numerous attempts to isolate a crystalline salt form of Compound A failed as only amorphous salts could be isolated. Additionally, the free base of Compound A was also isolated as an amorphous solid. The lack of a crystalline form of Compound A necessitated that Compound A had to be isolated from reaction mixtures by chromatography on silica gel. Separation from reaction impurities was tedious, large volumes of eluent were required, assay of dozens of fractions for concentration and purity was required and concentration of the desired fractions was time intensive. The product was isolated by chromatography on gram scale as an amorphous solid. Thus, development of a kilogram scale process requiring chromatographic separation would be expensive and time consuming, while scalability to a factory process was unknown but unlikely.

These problems were solved by identification of the crystalline pharmaceutically acceptable salts of Compound A of the present invention. More specifically, crystallization of pharmaceutically acceptable salts of Compound A directly from the crude or semi-purified reaction mixture obviates the need for chromatographic purification. This eliminates the tedious separation, large solvent requirements, and multiple assay requirements. Moreover, a crystallization process allows for more reproducible purity and yield upon scale up. Additionally, the crystalline tartrate salt of Compound A is isolated as a white, free-flowing solid allowing for easy isolation and manipulation. Still another advantage of the L-tartrate salt crystallization is that it enriches the chiral purity of Compound A.

Previous preparations of chiral Compound A were accomplished by following the teaching of PCT Int. Appl. WO 96/14846, wherein the racemic dihydropyrimidinone was converted to diastereomeric urea derivatives by treatment with 4-nitrophenyl chloroformate in the presence of base, followed by (R)-(+)-α-methyl benzylamine. The diastereomers were separated by chromatography on silica gel, then the chiral urea was cleaved to afford the desired (+)-dihydropyrimidinone isomer. This teaching essentially followed the prior art set forth by Atwal, et.al. (J. Med. Chem. 1990, 33, 2629) wherein this diastereomeric resolution was first described for a similar dihydropyrimidinone analog. In another report, Kappe et.al. (Tetrahedron 1992, 5473) have described the hydrogenolysis of a benzyl ester to afford the racemic acid derivative. The acid enantiomers were resolved by crystallization as the diastereomeric ammonium salts using either (R)-(+)-α-methyl benzylamine or (S)-(–)-α-methyl benzylamine.

The previously known methods for resolution of the dihydropyrimidinone suffer from several problems. The approach described in the teaching of PCT Int. Appl. WO 96/14846 or by Atwal, et. al. (J. Med. Chem. 1990, 33, 2629) requires a multi-step sequence for the preparation of diastereomers. These must then be separated by either fractional crystallization or chromatography on silica gel. Finally, the pure diasteromeric urea derivatives must be cleaved to their respective enantiomers and purified from the chiral resolving agent. In the method described by Kappe et.al. (Tetrahedron 1992, 5473) the ester substituent must be a benzyl group in order for effective hydrogenolysis to afford the carboxylic acid, which has been reported to be unstable. Following resolution by fractional crystallization, the salts were cleaved with acid to afford the pure acid enantiomers. If ester derivatives were desired, it was then necessary to esterify the carboxylic acid in an additional step. Since none of the chemical steps described in these processes are quantitative, each manipulation leads to a loss of product. Separation by chromatography on silica gel requires large volumes of solvent, multiple assays to determine purity of the collected fractions, and time consuming concentration of the desired fractions. Conditions for the fractional crystallization of either the diastereomeric ureas or diastereomeric ammonium salts must be determined for each derivative. Commonly, the yield for the multi-step resolution process was low.

The prior art methods depend on the efficiency of a chromatographic separation or fractional crystallization for their success. Slight variations in the purification conditions may easily lead to degradation of purity of the product. The multistep derivatization and separation sequence involves several chemical manipulations. The cost of obtaining the reagents and solvents, along with the costs of disposal or recovery of waste streams, is inefficient.

These problems of the prior art methods were solved by identification of the bioresolution process of the present invention. More specifically, the bioresolution process offers several advantages over these existing methodologies. It is a one step process, run in an aqueous media, which proceeds in high yield. This results in less wasted time and manpower for its practice, and requires a minimum amount of reagents, and solvents to perform.

SUMMARY OF THE INVENTION

The present invention provides a crystalline pharmaceutically acceptable salt of a compound A of the formula

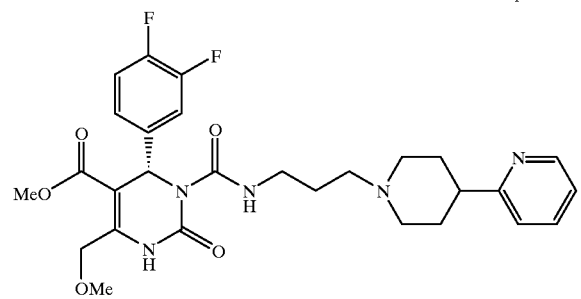

Compound A and solvates thereof.

In one embodiment of the invention is the crystalline pharmaceutically acceptable salt of Compound A, and solvates thereof, wherein the salt is selected from L-tartrate, D-tartrate, citrate or benzoate salts.

In a class of the invention is the crystalline salt of Compound A of the formula

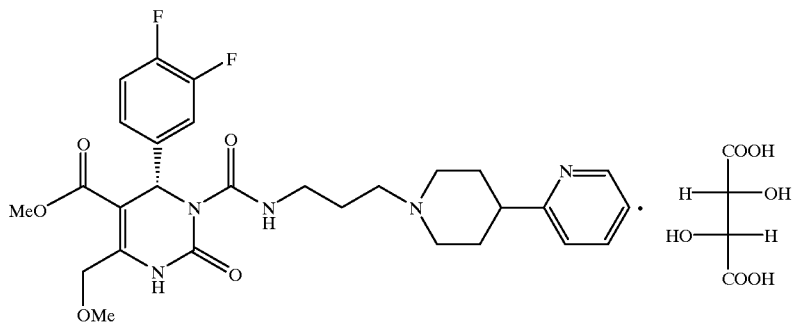

and solvates thereof.

In a subclass of the invention is the Compound A characterized by a differential scanning calorimetry (DSC) curve selected from:

(a) a DSC curve, at a heating rate of 10° C./min in an open cup under flowing nitrogen, exhibiting a relatively broad endotherm with an extrapolated onset temperature of about 56° C., a peak temperature of about 90° C. and an associated heat of about 23 J/gm followed by an endotherm with an extrapolated onset temperature of about 108° C., a peak temperature of about 115° C. and an associated heat of about 13 J/gm followed by an endotherm with an extrapolated onset temperature of about 145° C., a peak temperature of about 148° C. and an associated heat of about 57 J/gm; or (b) a DSC curve, at a heating rate of 10° C./min in an open cup under flowing nitrogen, exhibiting an endotherm with an extrapolated onset temperature of about 144° C., a peak temperature of about 148° C. and an associated heat of about 65 J/gm.

Illustrative of the invention is the Compound A characterized by an x-ray powder diffraction pattern selected from:

(a) an X-ray powder diffraction pattern characterized by d-spacings of 14.91, 8.32, 6.88, 5.41, 4.74, 4.29, 4.04, 3.86, 3.75 and 3.59 Å; or (b) an X-ray powder diffraction pattern characterized by d-spacings of 13.29, 7.82, 6.63, 6.20, 5.36, 5.01, 4.59, 4.35, 4.05, 3.73 and 3.60 Å.

An illustration of the invention is a pharmaceutical composition comprising the crystalline salt of Compound A, or solvate thereof, and a pharmaceutically acceptable carrier.

Exemplifying the invention is a pharmaceutical composition made by combining a crystalline salt of Compound A, or solvate thereof, and a pharmaceutically acceptable carrier.

Illustrating the invention is a process for making a pharmaceutical composition comprising combining a crystalline salt of Compound A, or solvate thereof, and a pharmaceutically acceptable carrier.

In another embodiment of the invention is the pharmaceutical composition further comprising a therapeutically effective amount of a testosterone 5-alpha reductase inhibitor. Preferably, the testosterone 5-alpha reductase inhibitor is a type 1, a type 2, both a type 1 and a type 2 (i.e., a three component combination comprising any of the compounds described above combined with both a type 1 testosterone 5-alpha reductase inhibitor and a type 2 testosterone 5-alpha reductase inhibitor) or a dual type 1 and type 2 testosterone 5-alpha reductase inhibitor. More preferably, the testosterone 5-alpha reductase inhibitor is a type 2 testosterone 5-alpha reductase inhibitor. Most preferably, the testosterone 5-alpha reductase inhibitor is finasteride.

Examples of the invention are methods of treating benign prostatic hyperplasia, of inhibiting contraction of prostate tissue and of relaxing lower urinary tract tissue in a subject in need thereof which comprises administering to the subject a therapeutically effective amount of any of the crysalline salts of Compound A, and solvates thereof, or pharmaceutical compositions described above. In another embodiment of the invention are the methods of treating BPH, of inhibiting contraction of prostate tissue and of relaxing lower urinary tract tissue in a subject in need thereof wherein the crystalline salt of Compound A, or solvate thereof, is administered in combination with a testosterone 5-alpha reductase inhibitor; preferably, the testosterone 5-alpha reductase inhibitor is finasteride.

Further illustrating the invention is a process for making a crystalline pharmaceutically acceptable salt of a compound of the formula

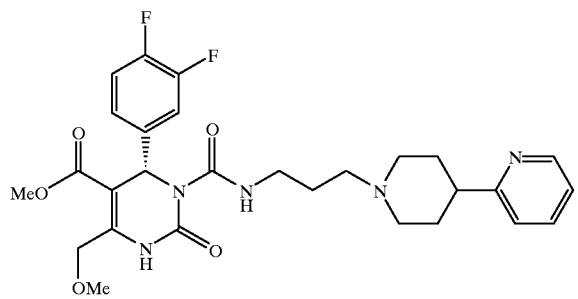

and solvates thereof, comprising the steps of:

(a) dissolving a free base compound of the formula

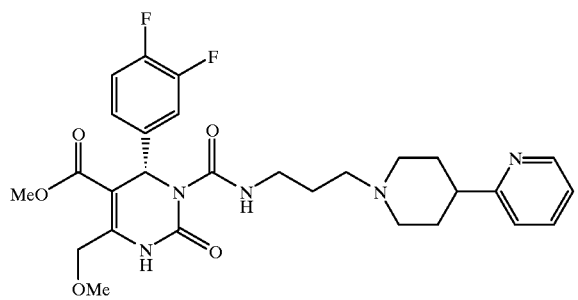

in a solvent to form a solution; and (b) treating the solution from step (a) with an acid to form the crystalline pharmaceutically acceptable salt. The term "treating," as used herein, includes both the process where the acid is added to the solution from step (a), as well as the process where the solution from step (a) is added to the acid.

An illustration of the invention is the process wherein the acid is a solution of the acid in a second solvent (which can be the same or different from the first solvent used to dissolve the free base of Compound A).

Further exemplifying the invention is the process wherein the acid is selected from L-tartaric acid, D-tartaric acid, citric acid or benzoic acid. Preferably, the acid is L-tartaric acid.

More particularly illustrating the invention is the process wherein the (first) solvent for dissolving Compound A free base and the (second) solvent for dissolving the acid are each independently selected from methanol, ethanol, 2-propanol, ethyl acetate, isopropyl acetate, butanol, hexanes, toluene or a mixture thereof. Preferably, the first and second solvents for dissolving Compound A free base and the acid, respectively, are each independently selected from ethanol, 2-propanol, or a mixture thereof.

More specifically exemplifying the invention is the process for making a crystalline pharmaceutically acceptable salt of a compound of the formula

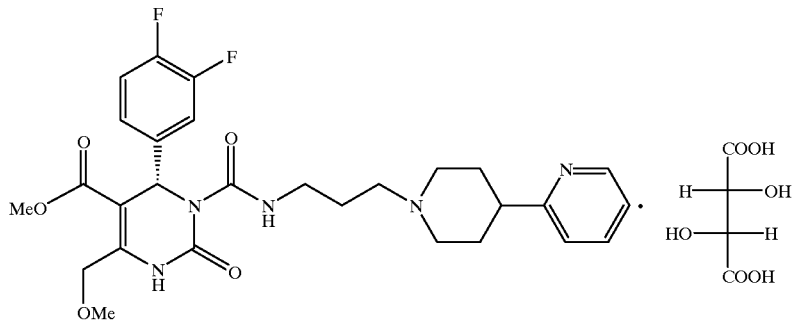

and solvates thereof, comprising the steps of:
(a) dissolving a free base compound of the formula

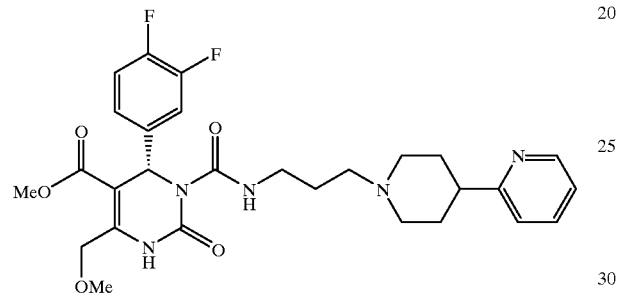

in a solvent selected from ethanol, 2-propanol, or a mixture thereof, to form a solution; and
(b) treating the solution from step (a) with L-tartaric acid to form the crystalline pharmaceutically acceptable salt of the formula

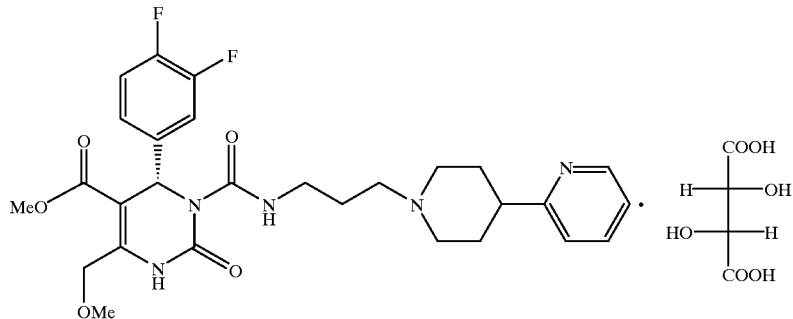

and solvates thereof.

More specifically illustrating the invention is a process for making a crystalline pharmaceutically acceptable salt of a compound of the formula

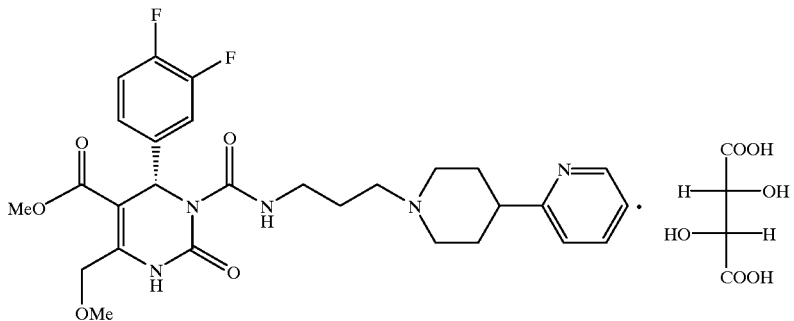

and solvates thereof, comprising the steps of:
(a) dissolving a free base compound of the formula

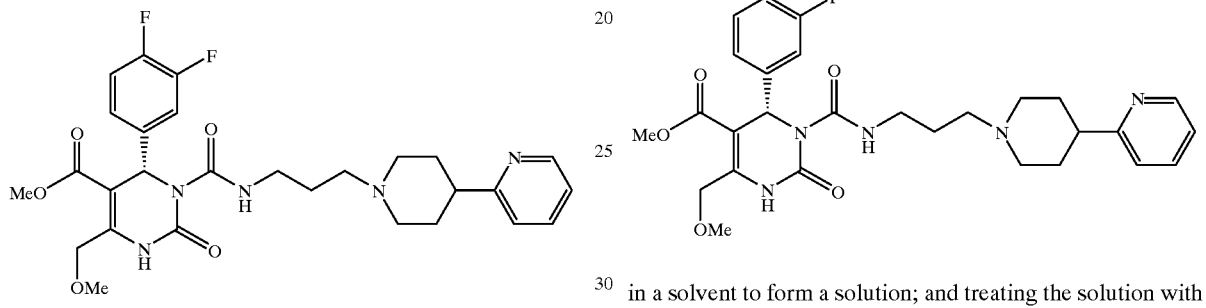

in a first solvent selected from methanol, ethanol, 2-propanol, ethyl acetate, isopropyl acetate, butanol, hexanes, toluene or a mixture thereof, to form a solution; and (b) treating the solution from step (a) with a solution of L-tartaric acid in a second solvent selected from methanol, ethanol, 2-propanol, ethyl acetate, isopropyl acetate, butanol, hexanes, toluene or a mixture thereof, to form the crystalline pharmaceutically acceptable salt of the formula

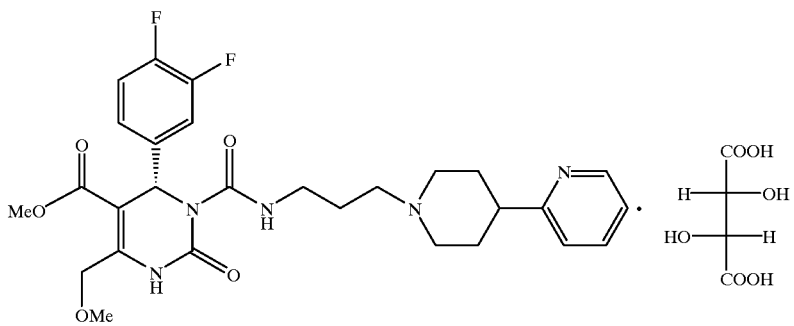

and solvates thereof.

An additional illustration of the invention is a crystalline pharmaceutically acceptable salt, and solvates thereof, made by any of the processes described above.

Still further exemplifying the invention is a crystalline pharmaceutically acceptable salt, and solvates thereof, made by dissolving a free base compound of the formula in a solvent to form a solution; and treating the solution with an acid selected from L-tartaric acid, D-tartaric acid, citric acid or benzoic acid to form the crystalline pharmaceutically acceptable salt. Preferably, the acid is L-tartaric acid.

An additional example of the invention is the use of any of the crystalline pharmaceutically acceptable salts of Compound A, and solvates thereof, described above in the preparation of a medicament for: a) the treatment of benign prostatic hyperplasia; b) relaxing lower urinary tract tissue; or c) inhibiting contraction of prostate tissue; in a subject in need thereof.

Another illustration of the invention is the use of any of the crystalline pharmaceutically acceptable salts of Compound A, and solvates thereof, described above and a 5-alpha reductase inhibitor for the manufacture of a medicament for: a) treating benign prostatic hyperplasia; b) relaxing urethral smooth muscle; or c) inhibiting contraction of prostate tissue which comprises an effective amount of the alpha 1a antagonist compound and an effective amount of 5-alpha reductase inhibitor, together or separately. Preferably, the 5-alpha reductase inhibitor is finasteride.

In another aspect of the invention is a crystalline salt of the compound of the formula

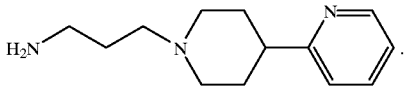

Preferably, the salt is selected from a L-tartrate, D-tartrate, citrate, benzoate salt, acetate, hydrochloride, sulfate, methane sulfonate or p-toluene sulfonate of (6). Most preferably, the crystalline compound of the formula

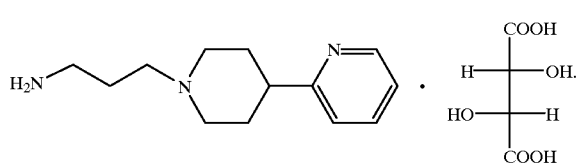

The present invention also provides a process to afford a compound of the formula IA

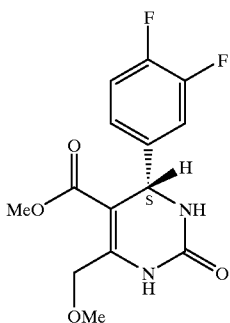

comprising the steps of
(a) contacting a racemic compound of the formula

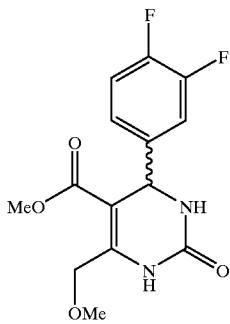

with a protease enzyme to form a mixture; and
(b) aging the mixture from step (a) to afford the compound IA.

In one embodiment of the invention is the process wherein the compound IA which is obtained is substantially free of its (R)-enantiomer. The term "substantially free of its R- enantiomer" means that the desired S- enantiomer is obtained in greater than about 75% ee (enantiomeric excess), preferably, greater than about 90% ee, and most preferably, greater than about 98% ee. Preferably, the compound IA is produced in greater than 75% ee. More preferably, the compound IA is produced in greater than 90% ee. Most preferably, the compound IA is produced in greater than 98% ee.

In a class of the invention is the process wherein the protease enzyme is selected from Proteinase K or a fungal enzyme produced by a closely related organism to *Tritirachium album* (the strain used to produce Proteinase K) or Subtilisin or a protease enzyme preparation obtained from *Metarhizium anisopliae* MF 6527. Preferably, the protease enzyme is Subtilisin.

In a subclass of the invention is the process further comprising the step of isolating the compound of formula I.

Illustrative of the invention is the process further comprising reacting the compound of formula IA.

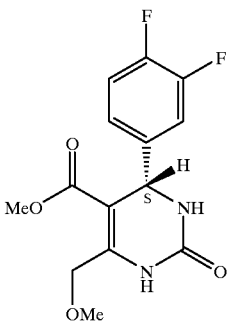

with 3-[4-(2-pyridyl)piperidin-1-yl]propylamine to form Compound A

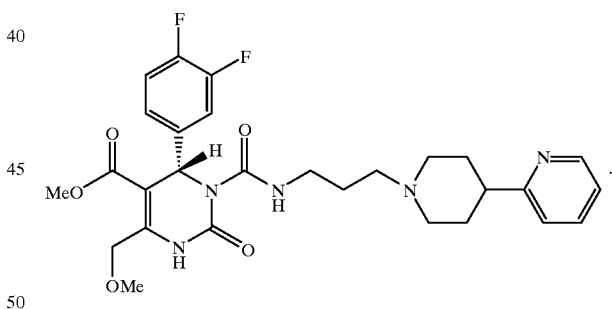

Illustrating the invention is the process wherein the reaction is aged for a period between about 1 day and about 3 weeks. Preferably, the reaction is aged for a period between about 5 and about 18 days.

Exemplifying the invention is the process wherein the reaction is aged at a pH between about 6 and about 9, preferably about 8.5.

An illustration of the invention is the process wherein the reaction is aged at a temperature between about 15° C. and about 50° C. Preferably, the reaction is aged at a temperature between about 30° C. to about 40° C. Most preferably, the reaction is aged at a temperature of about 37° C.

An example of the invention is a process to afford a compound of the formula IA

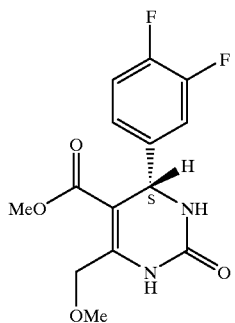

IA comprising the steps of
(a) contacting a racemic compound of the formula

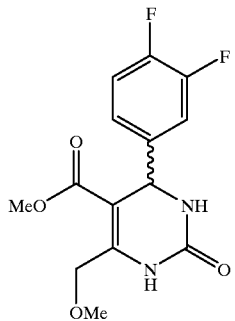

with water to form an aqueous mixture;
(b) contacting the aqueous mixture from step (a) with a polysaccharide gum to form an emulsion;
(c) contacting the emulsion from step (b) with a solvent selected from DMSO, iso-octane, isopropanol, methanol, hexane or acetonitrile to form a solvent mixture;
(d) contacting the solvent mixture from step (c) with a protease enzyme, preferably, a protease enzyme selected from Proteinase K or Subtilisin, to form a reaction mixture; and
(e) aging the reaction mixture from step (d) at a temperature between about 15° C. and about 50° C. for a period between about 1 day and about 3 weeks to afford the compound IA.

Further illustrating the invention is the process wherein the compound IA which is obtained is substantially free of its (R)-enantiomer. Preferably, the compound IA is produced in greater than 75% ee. More preferably, the compound IA is produced in greater than 90% ee. Most preferably, the compound IA is produced in greater than 98% ee.

Further exemplifying the invention is the process wherein the polysaccharide is selected from guar gum, arabic gum, or xanthan gum. Preferably, the polysaccharide is xanthan gum.

More particularly illustrating the invention is the process wherein the solvent is acetonitrile.

Another illustration of the invention is the process wherein the aqueous mixture from step (a) is buffered to a pH between about 6 and about 9, preferably about 8.5.

More specifically exemplifying the invention is the process wherein the reaction is aged for a period between about 5 and about 18 days.

An additional example of the invention is the process wherein the reaction is aged at a temperature between about 30° C. to about 40° C., preferably, about 37° C.

More specifically illustrating the invention is the process further comprising isolating the compound of formula IA.

More particularly exemplifying the invention is the process further comprising reacting the compound of formula IA

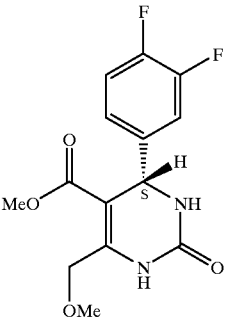

IA with 3-[4-(2-pyridyl)piperidin-1-yl]propylamine to form Compound A.

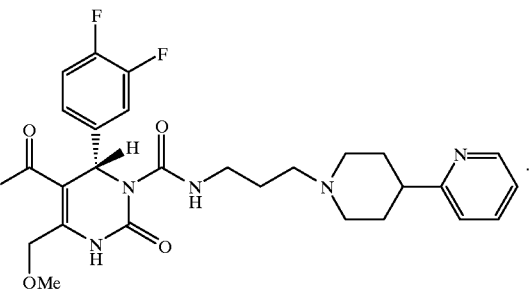

Compound A

In another aspect of the invention is a compound of the formula IA

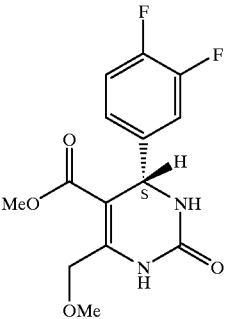

IA and salts thereof.

A further aspect of this invention is a chemical process for making a class of compounds of which Compound A is a member. This class of compounds can be represented by Formula (I):

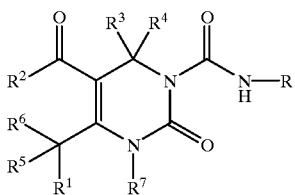

(I)

and it is prepared by treating a dihydropyrimidinone compound of Formula (II):

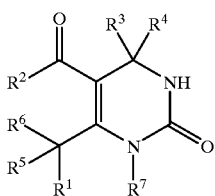

(II)

(the preparation of which is described in International Application WO97/21687, published Jun. 19, 1997) with a deprotonation agent, and contacting the deprotonated compound of Formula (II) with carbonyl diimidazole ("CDI"), followed by coupling the product of that reaction with an amine of Formula (III):

 (III)

Definitions for the groups R and R1 to R7 in the formulae are provided below.

The process of the invention offers significant advantages over the conventional procedure for coupling a primary amine and a dihydropyrimidinone. The conventional procedure involves the coupling of the amine with a 4-nitrophenylchloroformate derivative of the dihydropyrimidinone, which is itself prepared by deprotonating the dihydropyrimidinone with, for example, lithium diisopropylamide and then reacting the deprotonated compound with 4-nitrophenylchloroformate. When both the N1 and N3 positions on the dihydropyrimidinone are unsubstituted (i.e., hydrogen atoms are attached to the ring nitrogens), the conventional procedure typically provides poor selectivity between the N1 and N3 positions and often gives undesired bis-acylation. In addition, a large excess of base and 4-nitrophenylchloroformate (e.g., from about 3 to about 4 equivalents) is required to achieve good conversions. In sharp contrast, the process of the invention requires only a slight excess of CDI to achieve high conversions (e.g., greater than about 85% coupling), and, for dihydropyrimidinones having unsubstituted nitrogens, coupling occurs predominantly or exclusively at the N3 position, eliminating the need to protect and deprotect the N1 position to avoid the formation of bis-coupled products.

DETAILED DESCRIPTION OF THE INVENTION

The present invention provides crystalline pharmaceutically acceptable salts of the potent and selective alpha 1a adrenergic receptor antagonist, Compound A, pharmaceutical compositions containing them, and methods of making and using the crystalline pharmaceutically acceptable salts of Compound A. The crystalline pharmaceutically acceptable salts of Compound A and pharmaceutical compositions of the present invention are useful in eliciting an alpha 1a antagonizing effect, in the prevention and/or treatment of BPH, and in relaxing lower urinary tract tissue.

For use in medicine, the salts of the compounds of this invention refer to non-toxic "pharmaceutically acceptable salts." Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, citric acid, tartaric acid, carbonic acid or phosphoric acid.

The crystalline pharmaceutically acceptable salts of Compound A and pharmaceutical compositions of the present invention exhibit high selectivity for the human alpha 1a adrenergic receptor. One implication of this selectivity is that these compounds display selectivity for lowering intraurethral pressure without substantially affecting diastolic blood pressure.

The term "Compound A," as used herein refers to the free base shown below:

Compound A

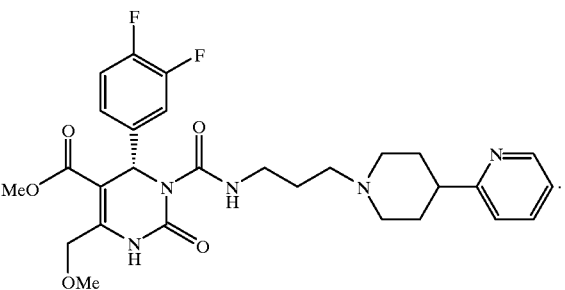

Compound A and its utility for antagonizing the alpha 1a adrenergic receptor, for treating BPH and for inhibiting lower urinary tract tissue is described in detail in WO 96/14846. Compound A is readily prepared according to the procedure of Example 30 in WO 96/14846, or according to the processes disclosed herein.

The term "selective alpha 1a adrenergic receptor antagonist," as used herein, refers to an alpha 1a antagonist compound which is at least ten fold selective for the human alpha 1a adrenergic receptor as compared to the human alpha 1b, alpha 1d, alpha 2a, alpha 2b and alpha 2c adrenergic receptors.

The term "lower urinary tract tissue," as used herein, refers to and includes, but is not limited to, prostatic smooth muscle, the prostatic capsule, the urethra and the bladder neck.

The term "subject," as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

The present invention also provides pharmaceutical compositions comprising the crystalline pharmaceutically acceptable salts of Compound A, and solvates thereof, in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

As used herein, the term "composition" is intended to encompass a product comprising the specified ingredients in the specified amounts, as well as any product which results, directly or indirectly, from combination of the specified ingredients in the specified amounts.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The invention involves the formation of crystalline pharmaceutically acceptable salts of the alpha 1a adrenergic receptor antagonist, Compound A, by treatment of the free base dissolved in a solvent with an acid. More specifically, the free base of Compound A is dissolved in a solvent and treated with about 0.5 to about 2.0 equivalents of the acid at a temperature of about 20 to about 80° C. to provide the crystalline salt of Compound A. Preferably, the free base of Compound A is dissolved in a solvent and treated with about 0.9 to about 1.3 equivalents of the acid at a temperature of about 35 to about 65° C. to provide the crystalline salt of Compound A. In a preferred embodiment, the free base of Compound A is dissolved in a solvent and treated with about 1.0 to about 1.1 equivalents of the acid at a temperature of about 45 to about 55° C. to provide the crystalline salt of Compound A. The acid is preferably selected from L-tartaric acid, D-tartaric acid, citric acid or benzoic acid. If desired, the acid can be added as a solution in a solvent which can be the same or different from the solvent used to dissolve the Compound A free base. In a particularly preferred embodiment, about 1.0 equivalent of L-tartaric acid is added to the solution of Compound A free base in the solvent at a temperature of about 50±10° C.

In the processes of making the crystalline pharmaceutically acceptable salts of the instant invention, the term "treating" or "treatment" which refers to the treatment of (or treating) Compound A in a solvent (i.e., "Compound A solution") with an acid, as used herein, includes both the addition of the acid to the Compound A solution, as well as the addition of the Compound A solution to the acid. That is, the order of addition is not important to the success of the process for forming the crystalline pharmaceutically acceptable salts of Compound A. In a preferred process, the acid is added to a solution of Compound A in a solvent.

A wide variety of solvents can be utilized as long as the Compound A free base is soluble in the solvent. Similarly, when the acid is added as a solution of the acid in a solvent, a wide variety of solvents can be used. Thus, suitable solvents for dissolving Compound A free base and/or the acid include, but are not limited to, water or esters, ketones, amides, ethers, alcohols and hydrocarbons, or mixtures thereof. Preferably, esters (e.g., ethyl acetate, isopropyl acetate), alcohols (e.g., methanol, ethanol, 2-propanol, butanol), hydrocarbons (e.g., hexanes, toluene) or mixtures thereof, are used as the solvent; more preferably, alcohols; most preferably, ethanol, or 2-propanol, or mixtures thereof, is utilized as the solvent. In a particularly preferred embodiment, 2-propanol is used as the solvent to provide the crystalline L-tartrate salt of Compound A.

Thus, one aspect of the invention involves the formation of a crystalline pharmaceutically acceptable salt of the alpha 1a adrenergic receptor antagonist, Compound A, by treatment of the free base in ethanol or 2-propanol at a temperature about 50±10° C. (preferably, about 50° C.), with L-tartaric acid in ethanol solution followed by crystallization. The resulting L-tartrate salt is isolated as a crystalline white, free-flowing solid. The L-tartrate salt has desirable pharmaceutical properties, such as bioavailability, tolerability, stability, low hygroscopicity and pH. In addition, the L-tartrate salt affords purification, enrichment of chiral purity and ease of handling of Compound A.

In general, the compounds of the present invention comprise Compound A as a crystalline pharmaceutically acceptable salt. In a preferred embodiment, the compound comprises a crystalline pharmaceutically acceptable salt of Compound A selected from the L-tartrate, D-tartrate, citrate or benzoate salts. In a particularly preferred embodiment, the compound comprises the crystalline L-tartrate salt of Compound A.

The compounds and pharmaceutical compositions of the present invention are useful in eliciting an alpha 1a antagonizing effect. Thus, the compounds and pharmaceutical compositions of this invention are useful in the prevention and/or treatment of BPH and for relaxing lower urinary tract tissue.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating BPH and for relaxing lower urinary tract tissue. The treatment involves administering to a patient in need of such treatment a crystalline pharmaceutically acceptable salt of Compound A, or a solvate thereof; or a pharmaceutical composition comprising a pharmaceutical carrier and a therapeutically effective amount of a crystalline pharmaceutically acceptable salt of Compound A of the present invention, or a solvate thereof.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

Compounds of this invention may be administered in any of the foregoing compositions and according to dosage regimens established in the art whenever specific blockade of the human alpha 1a adrenergic receptor is required.

The daily dosage of the products may be varied over a wide range from 0.01 to 1,000 mg per adult human per day. For oral administration, the compositions are preferably provided in the form of tablets containing 0.01, 0.05, 0.1, 0.5, 1.0, 2.5, 5.0, 10.0, 15.0, 25.0, 50.0, 100, 250 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. An effective amount of the drug is ordinarily supplied at a dosage level of from about 0.0002 mg/kg to about 20 mg/kg of body weight per day. Preferably, the range is from about 0.001 to 10 mg/kg of body weight per day, and especially from about 0.001 mg/kg to 7 mg/kg of body weight per day. The compounds may be administered on a regimen of 1 to 4 times per day. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Compounds of this patent disclosure may be used alone at appropriate dosages defined by routine testing in order to obtain optimal antagonism of the human alpha 1a adrenergic receptor while minimizing any potential toxicity. In addition, co-administration or sequential administration of other agents which alleviate the effects of BPH is desirable. Thus, in one embodiment, this includes administration of compounds of this invention and a human testosterone 5-α reductase inhibitor. Included with this embodiment are inhibitors of 5-alpha reductase iso enzyme 2. Many such compounds are now well known in the art and include such compounds as PROSCAR®, (also known as finasteride, a 4-Aza-steroid; see U.S. Pat. Nos. 4,377,584 and 4,760,071, for example). In addition to PROSCAR®, which is principally active in prostatic tissue due to its selectivity for human 5-α reductase isozyme 2, combinations of compounds which are specifically active in inhibiting testosterone 5-alpha reductase isozyme 1 and compounds which act as dual inhibitors of both isozymes 1 and 2, are useful in combination with compounds of this invention. Compounds that are active as 5α-reductase inhibitors have been described in WO93/23420, EP 0572166; WO 93/23050; WO93/23038; WO93/23048; WO93/23041; WO93/23040; WO93/23039; WO93/23376; WO93/23419, EP 0572165; WO93/23051.

The dosages of the alpha 1a adrenergic receptor and testosterone 5-alpha reductase inhibitors are adjusted when combined to achieve desired effects. As those skilled in the art will appreciate, dosages of the 5-alpha reductase inhibitor and the alpha 1a adrenergic receptor antagonist may be independently optimized and combined to achieve a synergistic result wherein the pathology is reduced more than it would be if either agent were used alone. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

Thus, in one preferred embodiment of the present invention, a method of treating BPH is provided which comprises administering to a subject in need of treatment any of the compounds of the present invention in combination with finasteride effective to treat BPH. The dosage of finasteride administered to the subject is about 0.01 mg per subject per day to about 50 mg per subject per day in combination with an alpha 1a antagonist. Preferably, the dosage of finasteride in the combination is about 0.2 mg per subject per day to about 10 mg per subject per day, more preferably, about 1 to about 7 mg per subject to day, most preferably, about 5 mg per subject per day.

For the treatment of benign prostatic hyperplasia, compounds of this invention exhibiting alpha 1a adrenergic receptor blockade can be combined with a therapeutically effective amount of a 5α-reductase 2 inhibitor, such as finasteride, in addition to a 5α-reductase 1 inhibitor, such as 4,7β-dimethyl-4-aza-5α-cholestan-3-one, in a single oral, systemic, or parenteral pharmaceutical dosage formulation. Alternatively, a combined therapy can be employed wherein the alpha 1a adrenergic receptor antagonist and the 5α-reductase 1 or 2 inhibitor are administered in separate oral, systemic, or parenteral dosage formulations. See, e.g., U.S. Pat. Nos. 4,377,584 and 4,760,071 which describe dosages and formulations for 5α-reductase inhibitors.

Abbreviations used in the instant specification, particularly the Schemes and Examples, are as follows:

Aq=aqueous
Ac=acetyl
CDI=carbonyl diimidazole
DMF=N,N-dimethylformamide
DMSO=dimethylsulfoxide
EtOH=ethanol
IPAc=isopropyl acetate
LDA=lithium diisopropylamide
Me=methyl
MeOH=methanol
MTBE=methyl tert-butyl ether
t-Bu=tertiary-butyl or tert-butyl
THF=tetrahydrofuran Additional abbreviations used in the instant specification, particularly in the Schemes, are as follows:

AcOH=acetic acid
BINAP=2,2'-Bis(diphenylphosphino)-1,1'-binaphthyl
Boc or BOC=t-butyloxycarbonyl
BOC$_2$O=di-tert-butyl dicarbonate
BuOH=butanol
n-BuLi=n-butyllithium
Cbz-Cl=benzyloxycarbonyl chloride
DPPA=diphenylphosphoryl azide
Et$_3$N=triethylamine
EtOAc=ethyl acetate
HPLC=high performance liquid chromatography
PCTLC (or PCC)=preparative centrifugal thin layer chromatography
Ph=phenyl
pTOS=p-toluenesulfonic acid
Tos$_2$O or TOS$_2$O=p-toluenesulfonic anhydride Compound A L-tartrate salt, i.e., (+)-5-Methoxycarbonyl-6-(3,4-difluorophenyl)-4-methoxy-carbonyl-1-{N-[3-(4-(2-pyridyl)piperidin-1-yl)propyl]}-carboxamido-1,2,3,6-tetrahydro-2-oxopyrimidine L-tartrate salt, (1) may be prepared according to Scheme 1. Racemic 2 is readily prepared from commercially available 3,4-difluorobenzaldehyde, methyl 4-methoxyacetoacetate, and urea following the teaching of PCT International Application Publication No. WO97/21687, published Jun. 19, 1997. Enantiomeric resolution to afford (+)-2 may be accomplished by conventional techniques known to those skilled in the art, or by removing (−)-2 via ester hydrolysis with commercially available protease enzyme, for example Subtilisin. (+)-2 is coupled with 3-[4-(2-pyridyl)piperidin-1-yl] propylamine, (6) (Scheme 2), utilizing carbonyl diimidazole, to afford (+)-5-methoxycarbonyl-6-(3,4-difluorophenyl)-4-methoxycarbonyl-1-{N-[3-(4-(2-pyridyl) piperidin-1-yl)propyl]} carboxamido-1,2,3,6-tetrahydro-2-oxopyrimidine, (3). Crystallization of the (+)-5-methoxycarbonyl-6-(3,4-difluorophenyl)-4-methoxycarbonyl-1-{N-[3-(4-(2-pyridyl)piperidin-1-yl) propyl]}carboxamido-1,2,3,6-tetrahydro-2-oxopyrimidine L-tartrate salt, (1) is accomplished by treating a solution of 3 with L-tartaric acid.

Scheme 1

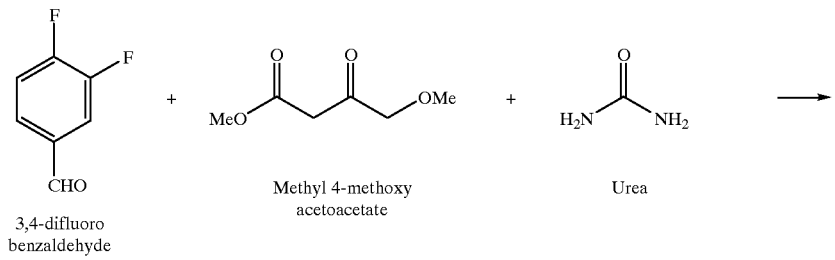

3,4-difluoro benzaldehyde

Methyl 4-methoxy acetoacetate

Urea

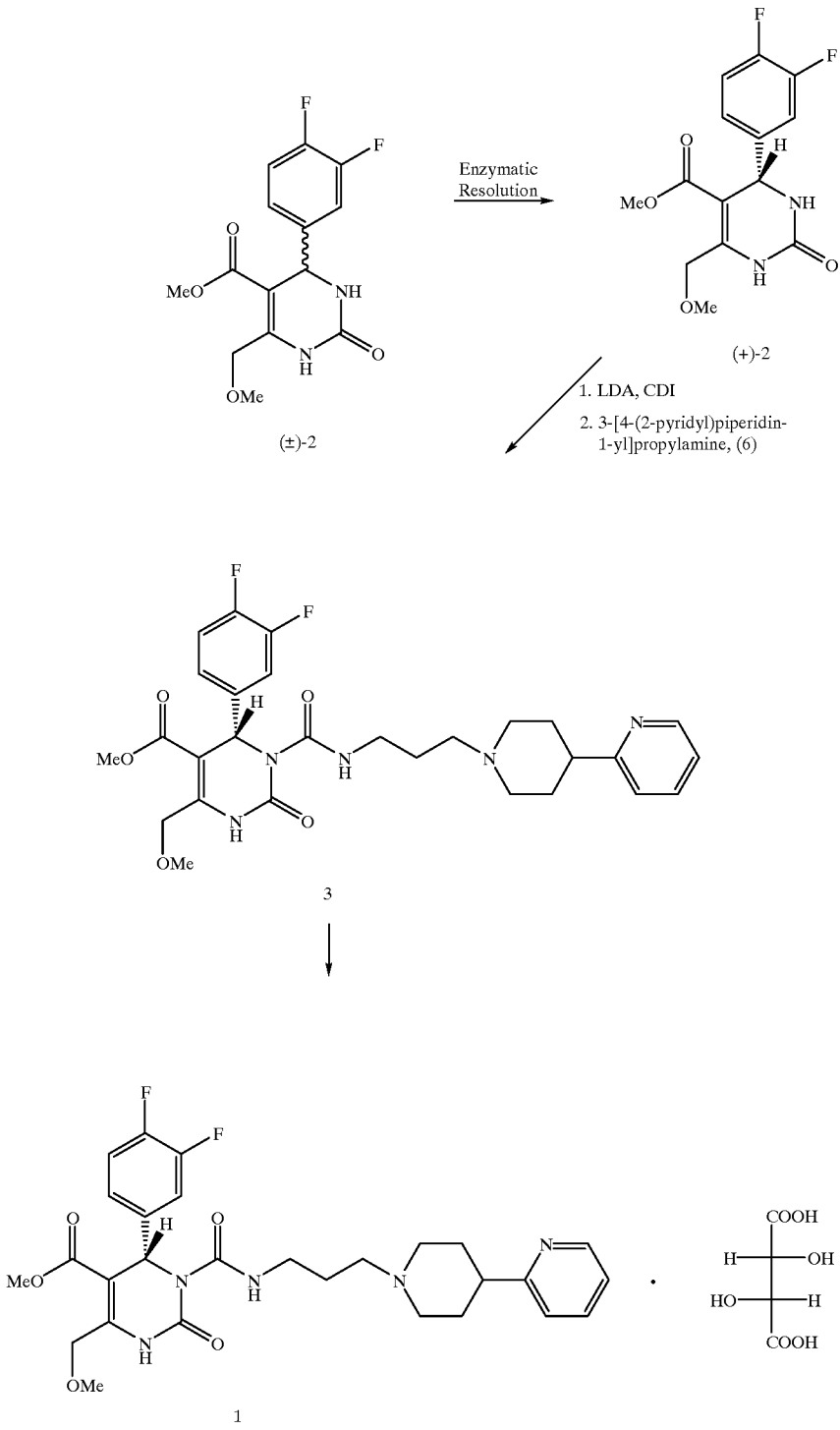

3-[4-(2-pyridyl)piperidin-1-yl]propylamine, (6) can be prepared following the teachings of WO 96/14846, or by the procedure outlined in Scheme 2 wherein commercially available 2,4'-dipyridyl is alkylated with 3-bromopropylamine hydrobromide to afford pyridinium salt 4. Reduction of 4 with sodium borohydride affords 5 which is hydrogenated over Pearlman's catalyst to afford 3-[4-(2-pyridyl)piperidin-1-yl]propylamine, (6). If desired, 6 may be used directly in the preparation of 3, or it may be crystallized as its L-tartrate salt 7.

Scheme 2

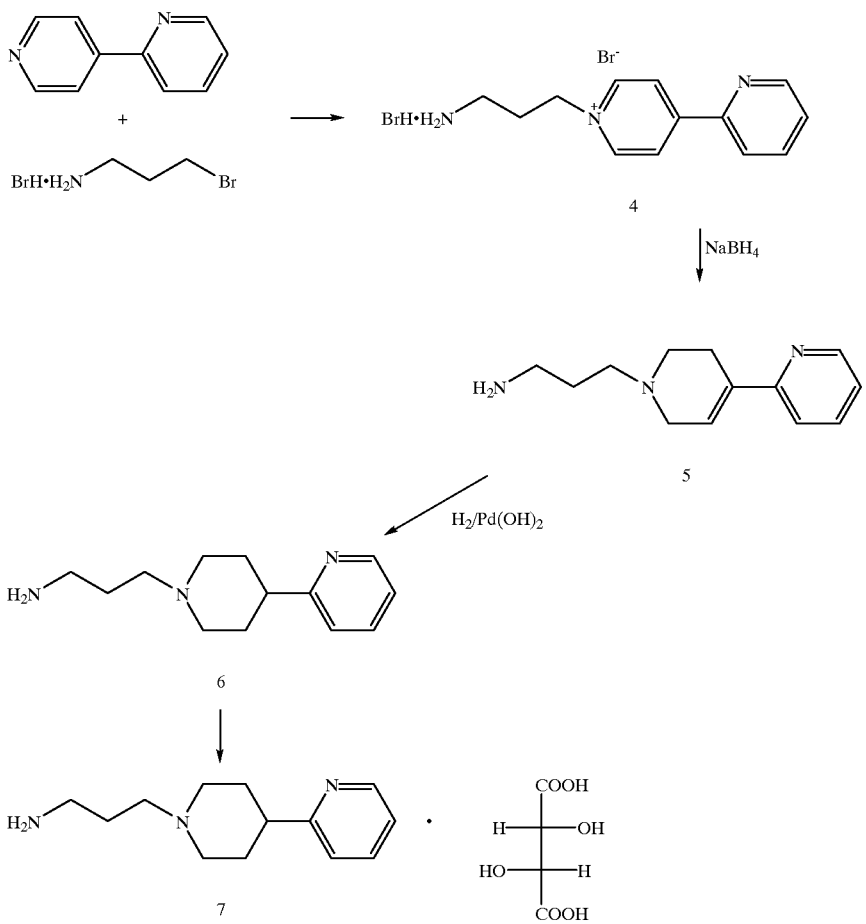

Thus, in another aspect of the invention is a crystalline salt of the side chain intermediate 3-[4-(2-pyridyl)piperidin-1-yl]propylamine, (6). The crystalline salts of intermediate 6 are prepared by treatment of the free base 6 dissolved in a solvent with an acid. More specifically, the free base is dissolved in a solvent and treated with about 0.5 to about 2 equivalents of an acid, which can be chosen from a mineral acid (such as HCl or $H_2SO_4$), a sulfonic acid (such as methane sulfonic acid or p-toluene sulfonic acid) or an organic acid (such as acetic acid, benzoic acid, citric acid, D- or L-tartaric acid) at a temperature of about 20 to about 100° C., preferably, about 50–80° C., most preferably, about 60–70° C., to provide the crystalline salt of 6. In a preferred embodiment of this aspect of the invention, the free base 6 is dissolved in a solvent and treated with about 0.8 to 1.5 equivalents of an organic acid, most preferably, about 1.0 to 1.1 equivalents of L-tartaric acid, to form the crystalline salt of 6. If desired, the acid can be added as a solution in a solvent which can be the same or different from the solvent used to dissolve the compound 6 free base. Additionally, the term "treating" or "treatment" which refers to the treatment of (or treating) the free base of 6 in a solvent with an acid, as used herein, includes both the addition of the acid to the solution of 6 in the solvent, as well as the addition of the Compound A solution to the acid. That is, the order of addition is not important to the success of the process for forming the crystalline salts of 6.

A wide variety of solvents can be utilized as long as intermediate 6 free base is soluble in the solvent. Similarly, when the acid is added as a solution of the acid in a solvent, a wide variety of solvents can be used. Thus, any common organic solvent such as, but not limited to, ethers, hydrocarbons, amides, alcohols, esters, ketones, or mixtures thereof. Preferably, esters (e.g., ethyl acetate, isopropyl acetate), alcohols (e.g., methanol, ethanol, 2-propanol, butanol), hydrocarbons (e.g., hexanes, toluene) or mixtures thereof, are used as the solvent; more preferably, alcohols; most preferably, ethanol is utilized as the solvent for dissolving intermediate 6 prior to treatment with the acid.

Crystallization of the side chain 6 as a salt affords several advantages. It allows for the removal of process impurities from the side chain in a convenient purification step without the need for a chromatographic purification. Typical silica gel chromatography is an inefficient process for purification in that it requires large amounts of eluent, assay of multiple fractions to determine purity, and time consuming concentration of the rich fractions to afford the product as a thick oil. This oil is difficult to assay, weigh, transfer, and handle as needed for subsequent steps. The crystalline salt is readily prepared from the crude side chain, it removes process impurities efficiently, and it is an easily isolated and handled material. These properties make its subsequent use more efficient.

The present invention also provides an improved process for making an alpha 1a adrenergic receptor antagonist useful for treating benign prostatic hyperplasia. More specifically, the invention provides an enzymatic resolution of a dihydropyrimidinone methyl ester which is an intermediate in the preparation of the alpha 1a adrenergic receptor, Compound A. Compound A and pharmaceutical compositions thereof are useful in eliciting an alpha 1a antagonizing effect, in the prevention and/or treatment of BPH, and in relaxing lower urinary tract tissue.

Compound A, and pharmaceutically acceptable salts thereof exhibit high selectivity for the human alpha 1a adrenergic receptor. One implication of this selectivity is that these compounds display selectivity for lowering intraurethral pressure without substantially affecting diastolic blood pressure.

The end product compounds (e.g., Compound A) synthesized from the intermediates of the present invention are useful in eliciting an alpha 1a antagonizing effect. Thus, the compounds and pharmaceutical compositions of this invention are useful in the prevention and/or treatment of BPH and for relaxing lower urinary tract tissue.

For these purposes, the end product compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

The daily dosage of the end product compounds made by the process of the present invention may be varied over a wide range from 0.01 to 1,000 mg per adult human per day. For oral administration, the compositions are preferably provided in the form of tablets containing 0.01, 0.05, 0.1, 0.5, 1.0, 2.5, 5.0, 10.0, 15.0, 25.0, 50.0, 100, 250 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. An effective amount of the drug is ordinarily supplied at a dosage level of from about 0.0002 mg/kg to about 20 mg/kg of body weight per day. Preferably, the range is from about 0.001 to 10 mg/kg of body weight per day, and especially from about 0.001 mg/kg to 7 mg/kg of body weight per day. The compounds may be administered on a regimen of 1 to 4 times per day. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The processes and intermediates of this invention are useful for the preparation of end-product compounds such as Compound A that are useful for antagonizing the alpha 1a adrenergic receptor, the prevention or treatment of BPH, for inhibiting contraction of prostate tissue and for relaxing lower urinary tract tissue.

The term "contacting," as used herein, refers to the step of combining two or more reactants (i.e., contacting two or more reactants with each other) where the order of addition of the reactants is not important. Thus, for example, in the step of "contacting a racemic compound (±)-2 with water," the term "contacting" means that the (+)-2 can be added to water, or that the water can be added to (±)-2.

The term "aging," as used herein, refers to the step of allowing the reactants (e.g., protease enzyme and racemate (±)-2) to stay in contact with each other.

The invention involves a process for producing (+)-(S)-dihydropyrimidinone (DHP) methyl ester, i.e., (+)-2, from the racemate by resolution using proteases as shown in Scheme 3.

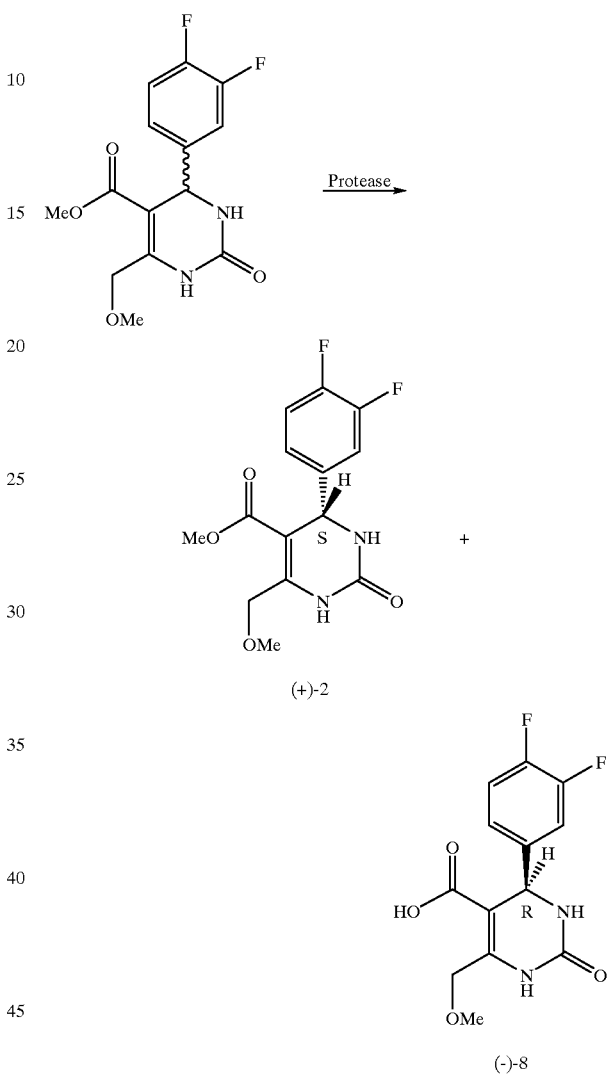

In general, an amount of racemic ester (±)-2 is added to water which may or may not be buffered at a pH between about 6 and about 9, preferably about 8.5. The aqueous ester (±)-2 mixture may optionally be blended with 10 g/l or less of a polysaccharide gum to form an emulsion. Any polysaccharide gum known to one of ordinary skill in the art may be used; preferably, the gum is selected from guar gum, arabic gum, or xanthan gum; most preferably, xanthan gum. A water-miscible or water-immiscible organic solvent, such as DMSO, iso-octane, isopropanol, methanol, hexane, or preferably, acetonitrile, may optionally be added at a concentration of about 20% or less, preferably a concentration of about 9%. A protease enzyme, such as Proteinase K or a fungal enzyme produced by a closely related organism to *Tritirachium album* (the strain used to produce Proteinase K) or Subtilisin or a protease enzyme preparation obtained from *Metarhizium anisopliae* MF 6527, is added. The resulting reaction is stirred and allowed to age at a temperature between about 15° C. and about 50° C., preferably about 30°

C. to about 40° C., most preferably about 37° C., for a period of time of between about 1 day and about 3 weeks, preferably, between about 5 and about 18 days, or until a desired degree of resolution has been achieved.

Metarhizium anisopliae, MF6527, is in the culture collection of Merck & Co., Inc., Rahway, N.J. A sample of the Metarhizium anisopliae MF6527 was deposited under the Budapest Treaty at the American Type Culture Collection (ATCC), 10801 University Boulevard, Manassas, Va. 20110-2209 on Jul. 30, 1998. The culture access designation is ATCC 74459. This deposit will be maintained in the ATCC for at least 30 years and will be made available to the public upon the grant of a patent disclosing it. The availability of a deposit does not constitute a license to practice the subject invention in derogation of patent rights granted by government action.

The protease-producing fungus is a strain Metarhizium anisopliae (MF6527, GB5475) which was isolated from soil collected in secondary vegetation of a tropical dry forest, Guanacaste National Park, Guanacaste Province, Costa Rica. The fungus is readily identified by its production of compact, dry, dark green sporodochia on agar culture media, eg., cornmeal agar or malt extract agar. Microscopically the fungus produces complex, pencillately branched condiophores that give rise to ampulliform, phialidic condiogenesis cells. Conidia are dry, elliptical, smooth and formed in dry chains. The strain conforms in all aspects to modern descriptions of Metarhizium anisopliae (e.g. K. H. Domsch, W. Gams, & T.-H. Anderson. 1980. Compendium of Soil Fungi. Vol. 1., Academic Press, London, U.K. pg. 413).

The processes of the present invention provide (+)-S-2 substantially free of its (−)-R-2 enantiomer. The term "substantially free of its (−)-R-2 enantiomer" means that the desired (+)-S-2 enantiomer is obtained in greater than about 75% ee (enantiomeric excess), preferably, greater than about 90% ee, and most preferably, greater than about 98% ee.

The end product Compound A L-tartrate salt, i.e., (+)-5-Methoxycarbonyl-6-(3,4-difluorophenyl)-4-methoxycarbonyl-1-{N-[3-(4-(2-pyridyl)piperidin-1-yl)propyl]}-carboxamido-1,2,3,6-tetrahydro-2-oxopyrimidine L-tartrate salt, (1) may be prepared according to Scheme 1 as described above.

The present invention further provides a chemical process for making a class of dihydropyrimidinone compounds of which Compound A is a member. The process for the preparation of a compound of Formula (I):

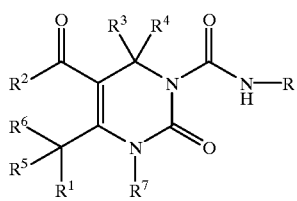

(I)

comprises treating a dihydropyrimidinone of Formula (II):

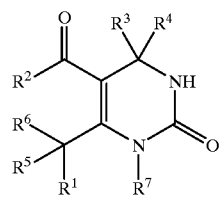

(II)

with a deprotonation agent; then contacting the treated dihydropyrimidinone with 1,1'-carbonyldiimidazole to form an acylimidazolide intermediate; and then contacting the acylimidazolide intermediate with an amine of Formula (III):

$$H_2N-R \quad (III)$$

to form the compound of Formula (I); wherein $R^1$, $R^5$ and $R^6$ are each independently selected from:
1) hydrogen,
2) halogen,
3) $C_{1-10}$ alkyl,
4) $C_{3-8}$ cycloalkyl,
5) substituted $C_{1-10}$ alkyl, wherein the substituents are independently selected from halogen, $C_{1-6}$ alkoxy, halogen-substituted $C_{1-6}$ alkoxy, $C_{3-6}$ cycloalkyl, phenyl, and halogen-substituted phenyl,
6) substituted $C_{3-8}$ cycloalkyl, wherein the substituents are independently selected from halogen, $C_{1-6}$ alkoxy, halogen-substituted $C_{1-6}$ alkoxy, $C_{1-6}$ alkyl, halogen-substituted $C_{1-6}$ alkyl, phenyl, and halogen-substituted phenyl,
7) phenyl, and
8) substituted phenyl, wherein the substituents are independently selected from halogen, $C_{1-4}$ alkyl, halogen-substituted $C_{1-4}$ alkyl, cyano, nitro, and $C_{1-4}$ alkoxy; or $R^1$ is as defined above and $R^5$ and $R^6$ together form a 3- to 7-membered saturated or unsaturated carbocyclic ring or a 4- to 7-membered saturated or unsaturated heterocyclic ring, the carbocyclic ring or heterocyclic ring optionally substituted with $C_{1-6}$ alkyl, wherein the heterocylic ring contains from 1 to 3 heteroatoms independently selected from nitrogen, oxygen, and sulfur, $R^2$ is:
1) hydrogen,
2) hydroxy,
3) $C_{1-10}$ alkyl,
4) halogen-substituted $C_{1-10}$ alkyl,
5) $C_{1-6}$ alkoxy,
6) halogen-substituted $C_{1-6}$ alkoxy,
7) $C_{3-6}$ cycloalkyl, or
8) substituted $C_{3-6}$ cycloalkyl, wherein the substituents are independently selected from halogen, hydroxy, $C_{1-6}$ alkyl, halogen-substituted $C_{1-6}$ alkyl, and $C_{1-6}$ alkoxy;

$R^3$ and $R^4$ are each independently selected from hydrogen, $C_{1-10}$ alkyl, and the group of Formula (IV):

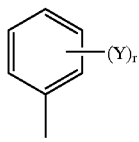

(IV)

wherein each Y is independently selected from
1) halogen,
2) cyano,
3) $C_{1-6}$ alkoxy,
4) nitro,
5) $C_{1-10}$ alkyl, and
6) halogen-substituted $C_{1-10}$ alkyl;

r is an integer of from 0 to 5;

$R^7$ is selected from hydrogen and $C_{1-10}$ alkyl; and

R is selected from $C_{1-40}$ hydrocarbyl and substituted $C_{1-40}$ hydrocarbyl.

In the process of the invention:

$R^1$, $R^5$ and $R^6$ are preferably each independently selected from hydrogen; halogen; $C_{1-4}$ alkyl; and substituted $C_{1-4}$ alkyl, wherein the substituents are independently selected from halogen, $C_{1-4}$ alkoxy, and halogen-substituted $C_{1-4}$ alkoxy; and more preferably $R^5$ and $R^6$ are hydrogen and $R^1$ is hydrogen, $C_{1-4}$ alkyl, or $C_{1-4}$ alkoxy.

$R^2$ is preferably hydrogen, $C_{1-4}$ alkyl, halogen-substituted $C_{1-4}$ alkyl, or $C_{1-4}$ alkoxy; is more preferably $C_{1-4}$ alkyl or $C_{1-4}$ alkoxy; and is most preferably $C_{1-4}$ alkoxy (e.g., methoxy).

$R^3$ and $R^4$ are preferably each independently selected from hydrogen, $C_{1-4}$ alkyl, and the group of Formula (IV):

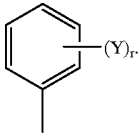

(IV)

More preferably, $R^4$ is hydrogen and $R^3$ is selected from $C_{1-4}$ alkyl and the group of Formula (IV). Most preferably, $R^4$ is hydrogen and $R^3$ is the group of Formula (IV). Y in Formula (IV) is preferably selected from halogen, cyano, $C_{1-4}$ alkoxy, nitro, $C_{1-4}$ alkyl, and halogen-substituted $C_{1-4}$ alkyl; and is more preferably selected from hydrogen, fluorine, cyano, $C_{1-4}$ alkyl, and trifluoromethyl. r is preferably an integer from 0 to 3, and more preferably an integer from 0 to 2.

In another preferred embodiment of the process of the invention, $R^4$, $R^5$, and $R^6$ are each hydrogen.

$R^7$ is preferably selected from hydrogen and $C_{1-4}$ alkyl, and is more preferably hydrogen.

R is preferably selected from
1) $C_{1-16}$ alkyl,
2) substituted $C_{1-16}$ alkyl wherein the substituents are independently selected from halogen, hydroxy, $C_{3-8}$ cycloalkyl, $C_{1-4}$ alkoxy, cyano, nitro, $NHR^a$, and $N(R^a)_2$,
3) $C_{5-7}$ cycloalkyl,
4) substituted $C_{5-7}$ cycloalkyl, wherein the substituents are independently selected from halogen, hydroxy, $C_{1-10}$ alkyl, $C_{1-4}$ alkoxy, cyano, nitro, $NHR^a$, and $N(R^a)_2$,
5) phenyl,
6) substituted phenyl, wherein the substituents are independently selected from halogen, $C_{1-4}$ alkyl, halogen-substituted $C_{1-4}$ alkyl, cyano, nitro, and $C_{1-4}$ alkoxy, and
7) the group represented by Formula (V):

(V)

wherein $R^8$ and $R^9$ are independently selected from
1) hydrogen,
2) $C_{1-4}$ alkyl, and
3) $C_{5-7}$ cycloalkyl;

$R^{10}$ is independently selected from

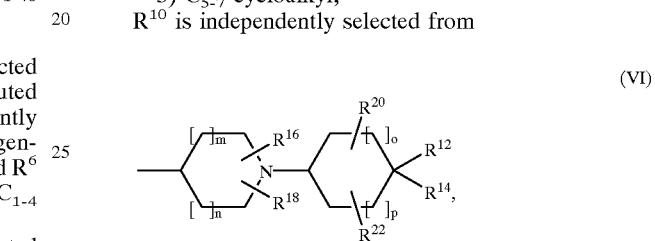

(VI)

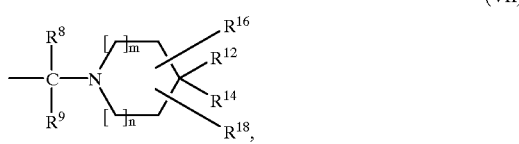

(VII)

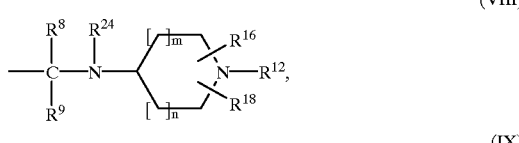

(VIII)

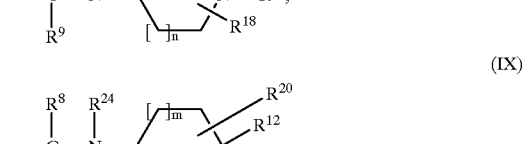

(IX)

and

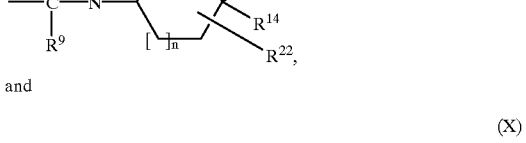

(X)

wherein $R^{12}$ is selected from
1) phenyl,
2) substituted phenyl, wherein the substituents on the phenyl are independently selected from halogen, hydroxy, trifluoromethyl, cyano, nitro, $C_{1-4}$ alkyl, $C_{1-4}$ alkoxy, $NH^a$, and $N(R^a)_2$, and
3) unsubstituted or substituted pyridyl, pyridyl N-oxide (N->O), pyrazinyl, thienyl, thiazolyl, furanyl, quinazolinyl, or naphthyl wherein the substituents thereon are independently selected from halogen, trifluoromethyl, cyano, nitro, $C_{1-4}$ alkyl, $C_{1-4}$ alkoxy, phenyl, $C_{3-8}$ cycloalkyl, $NHR^a$, and $N(R^a)_2$;

$R^{14}$ is selected from
1) hydrogen,
2) cyano,
3) $C_{1-4}$ alkyl,
4) $OR^b$,
5) $CO_2R^b$,
6) $CON(R^a)_2$,
7) phenyl,
8) substituted phenyl wherein the substituents on the phenyl are independently selected from halogen, trifluoromethyl, cyano, nitro, $C_{1-4}$ alkyl, $C_{1-4}$ alkoxy, $NHR^a$, and $N(R^a)_2$, and
9) unsubstituted or substituted pyridyl, thienyl, furanyl or naphthyl wherein the substituents thereon are independently selected from trifluoromethyl, phenyl, halogen, $C_{1-4}$ alkyl, $C_{1-4}$ alkoxy, and $C_{3-8}$ cycloalkyl;

$R^{16}$, $R^{18}$, $R^{20}$ and $R^{22}$ are each independently selected from hydrogen, $C_{1-10}$ alkyl, $C_{3-8}$ cycloalkyl, $(CH_2)_{0-4}OR^a$, $(CH_2)_{0-4}CF_3$, $(CH_2)_{0-4}CO_2R^a$, $(CH_2)_{0-4}CN$, $(CH_2)_{0-4}NHR^a$, and $(CH_2)_{0-4}N(R^a)_2$;

$R^{24}$ is selected from hydrogen, $C_{1-4}$ alkyl, and $C_{5-7}$ cycloalkyl;

$R^a$ is $C_{1-4}$ alkyl;

$R^b$ is hydrogen, $C_{1-4}$ alkyl, $C_{3-8}$ cycloalkyl, or $(CH_2)_{1-4}CF_3$;

m, n, o, and p are each independently selected from 0, 1, and 2, with the proviso that the sum of m+n and the sum of o+p are independently never greater than 3; and q is an integer from 0 to 4

R is more preferably selected from
1) $C_{3-12}$ alkyl,
2) substituted $C_{3-12}$ alkyl wherein the substituents are independently selected from halogen, hydroxy, $C_{1-4}$ alkoxy, cyano, and nitro,
3) $C_{5-7}$ cycloalkyl,
4) substituted $C_{5-7}$ cycloalkyl, wherein the substituents are independently selected from halogen, hydroxy, $C_{1-4}$ alkyl, $C_{1-4}$ alkoxy, cyano, and nitro,
5) substituted phenyl, wherein the substituents are independently selected from halogen, $C_{1-4}$ alkyl, halogen-substituted $C_{1-4}$ alkyl, cyano, nitro, and $C_{1-4}$ alkoxy; and
6) the group of Formula (V):

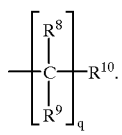

(V)

R is still more preferably the group of Formula (V). $R^8$ and $R^9$ are preferably independently selected from hydrogen and $C_{1-4}$ alkyl. More preferably $R^8$ is hydrogen and $R^9$ is $C_{1-4}$ alkyl, and most preferably $R^8$ and $R^9$ are both hydrogen.

$R^{10}$ is preferably independently selected from the structure of Formula (VI) and the structure of Formula (VII).

In $R^{10}$, $R^{12}$ is preferably selected from phenyl; substituted phenyl, wherein the substituents on the phenyl are independently selected from halogen, trifluoromethyl, cyano, nitro, $C_{1-4}$ alkyl, and $C_{1-4}$ alkoxy; and unsubstituted or substituted pyridyl wherein the substituents on the pyridyl are independently selected from halogen, trifluoromethyl, cyano, nitro, $C_{1-4}$ alkyl, and $C_{1-4}$ alkoxy. In another preferred embodiment, $R^{12}$ is substituted phenyl wherein the substituents are independently selected from fluorine, cyano, $C_{1-4}$ alkyl, and trifluoromethyl, wherein the number of substituents on the phenyl is from 1 to 3, preferably from 1 to 2.

$R^{14}$ is preferably selected from hydrogen; cyano; $C_{1-4}$ alkyl; $OR^b$; phenyl; substituted phenyl wherein the substituents on the phenyl are independently selected from halogen, trifluoromethyl, cyano, nitro, $C_{1-4}$ alkyl, and $C_{1-4}$ alkoxy; and unsubstituted or substituted pyridyl wherein the substituents on the pyridyl are independently selected from trifluoromethyl, phenyl, halogen, $C_{1-4}$ alkyl, and $C_{1-4}$ alkoxy. In another preferred embodiment, $R^{14}$ is selected from hydrogen, cyano, $C_{1-4}$ alkyl and $OR^b$.

$R^{16}$, $R^{18}$, $R^{20}$ and $R^{22}$ are preferably each independently selected from hydrogen, $C_{1-4}$ alkyl, $(CH_2)_{0-4}OR^a$, $(CH_2)_{0-4}CF_3$, $(CH_2)_{0-4}CO_2R^a$, and $(CH_2)_{0-4}CN$; and more preferably selected from hydrogen and $C_{1-4}$ alkyl. In a preferred embodiment, $R^{16}$, $R^{18}$, $R^{20}$ and $R^{22}$ are all hydrogen.

$R^{24}$ is preferably selected from hydrogen and $C_{1-4}$ alkyl, and is more preferably hydrogen.

$R^a$ is preferably methyl or ethyl.

$R^b$ is preferably hydrogen or $C_{1-4}$ alkyl, and is more preferably hydrogen, methyl, or ethyl.

q is preferably 2 or 3.

In the process of the invention the compound of Formula (I) is prepared by treating a compound of Formula (II) with a deprotonation agent and then contacting the treated compound of Formula (II) with carbonyl diimidazole, followed by coupling the product thereof with an amine of Formula (III). The deprotonation agent is an organic or inorganic compound which is sufficiently basic to accept and bind a proton under the reaction conditions. In one embodiment, the deprotonation agent is selected from the group consisting of alkali metal carbonates and bicarbonates, alkali metal salts of di -$C_{1-4}$ alkylamines, alkali metal salts of $C_{1-6}$ hydrocarbons (i.e., methane, ethane, and the linear and branched propanes, butanes, pentanes and hexanes), and alkali metal salts of bis(tri-$C_{1-4}$ alkylsilyl)amines. Suitable deprotonation agents include, but are not limited to, lithium diisopropylamide ("LDA"), lithium bis(trimethylsilyl) amide, and butyllithium. LDA is a preferred deprotonation agent for the process of the invention.

The deprotonation step is typically conducted by treating a the dihydropyrimidinone compound of Formula (II) dissolved or suspended in an inert solvent (e.g., aromatic hydrocarbons such toluene, xylene, and ethylbenzene; alkyl ethers such as ethyl ether or THF; aliphatic hydrocarbons such as pentane, hexane, or heptane; and mixtures thereof) with the deprotonation agent (e.g., LDA as either a solid or dissolved or suspended in an aliphatic hydrocarbon, an aromatic hydrocarbon, and/or an ether) for a suitable time and at a suitable temperature for the deprotonation of the dihydropyrimidinone compound. The order of addition is not important here; i.e., the term "treating" here involves either adding the deprotonation agent to the dihydropyrimidinone compound or vice versa. The temperature is suitably in the range of from about −80 to about 25° C., typically in the range of from about −70 to about −25° C., and preferably in the range of from about −70 to about −40° C. (e.g., from about −65 to about −55° C.). While the reaction time (i.e., treating time) can vary widely depending upon the choice of reaction temperature, deprotonation agent, and the particular dihydropyrimidinone reactant employed, it is typically in the range of from about 5 minutes to about 5 hours, and more typically in the range of from about 15 minutes to about 2 hours (e.g., from about 10 to about 30 minutes).

Following deprotonation, the deprotonation reaction mixture is contacted with CDI. The term "contacting" here means that either the CDI is added to the reaction mixture or the reaction mixture is added to the CDI. It is more typical to add the CDI to the reaction mixture. The CDI is typically employed as a solid, although a solution or suspension of CDI in an inert solvent such as THF, toluene, or heptane may be used instead. The resulting mixture is allowed to react at a temperature suitably in the range of from about −80 to about 40° C., and typically in the range of from about −70 to about 30° C. (e.g. from about −65 to about 25° C.) for a time sufficient to form the acyl imidazolide. The reaction time is suitably in the range of from about 30 minutes to about 5 hours, and typically in the range of from about 30 minutes to about 3 hours (e.g., from about 45 minutes to about 2 hours). The formation of the acylimidazolide can be monitored by HPLC, and the reaction is typically carried out until at least a major portion of the starting dihydropyrimidinone compound has been converted to acyl imidazolide. The degree of conversion of dihydropyrimidinone to imidazolide is typically at least about 60%, more typically at least about 80%, and preferably at least about 90%.

Subsequent to the acylimidazolide formation step, the acylimidazolide-containing reaction mixture is contacted with an amine of Formula (III), either by addition of the amine to the reaction mixture or vice versa, to form the compound of Formula (I). It is more typical to add the amine to the reaction mixture. An amine salt of an organic (e.g., aliphatic carboxylic acids such as acetic acid) or inorganic acid (e.g., HCl or HBr) may optionally be used in place of the amine itself. The amine is typically dissolved or suspended in an inert solvent (e.g., aliphatic hydrocarbons such as pentane, hexane, and/or heptane; ethers such as alkyl ethers—ethyl ether—and/or THF, alkyl acetates such as isopropyl acetate). The coupling of the amine to the dihydropyrimidinone is typically conducted at a temperature in the range of from about −80 to about 40° C., and more typically in the range of from about −70 to about 30° C. (e.g. from about 15 to about 25° C.). In one embodiment, the reaction mixture is at a relatively low temperature during the addition of the amine (e.g., from about −80 to about −20° C.) and, upon completion of amine addition, is then increased to a relatively high temperature (e.g., from about 0 to about 25° C. ). The coupling can be monitored by HPLC analysis and is typically conducted until at least a major portion of the acyl imidazolide has been converted to the coupled amine product. The degree of conversion of imidazolide to coupled product is typically at least about 70%, more typically at least about 85%, and preferably at least about 90%.

After the coupling reaction is completed, the reaction is quenched, typically by the addition of water. The desired compound of Formula (I) can be recovered via conventional separation techniques such as extraction, chromatography, and crystallization.

In the deprotonation step, the deprotonation agent is suitably employed in an amount of from about 0.8 to about 2.0 equivalents, typically in an amount of from about 1.0 to about 1.5 equivalents, and preferably in an amount of from about 1.0 to about 1.3 equivalents, per equivalent of the dihydropyrimidinone compound of Formula (II).

In the acylimidazolide formation step, CDI is employed in an amount of at least about 1 equivalent, and is suitably in the range of from about 1.0 to about 1.5 equivalents of CDI, and is preferably in the range of from about 1.1 to about 1.3 equivalents (e.g., 1.2 equivalents) of CDI, per equivalent of compound (II). An advantage of the process of the invention is that only a slight excess of CDI is typically required (e.g., from about 1.1 to about 1.5 equivalents of CDI per equivalent of compound (I)) to achieve high rates of conversion (e.g., greater than about 85%). When $R^7$ is hydrogen (i.e., when both the N-1 and N-3 positions on the dihydropyrimidinone ring are unsubstituted), a further advantage of the process of the invention is that the acyl imidazolide forms predominantly or exclusively at the N-3 position of the dihydropyrimidinone ring, so that no deprotection/ protection steps are required to prevent coupling at the N-1 position.

In the coupling step, the amine is suitably employed in an amount of from about 1.0 to about 2.5 equivalents, typically in an amount of from about 1.1 to about 2.0 equivalents, and preferably in an amount of from about 1.1 to about 1.5 equivalents (e.g., from about 1.2 to about 1.5 equivalents), per equivalent of the dihydropyrimidinone compound of Formula (II).

Conversions of at least about 50% (e.g., from about 80% to about 99%) of the starting dihydropyrimidinone to coupled amine product can be achieved via the process of the invention.

In a particular illustration of the process of the invention, a process for preparing a dihydropyrimidinone compound of Formula (XI):

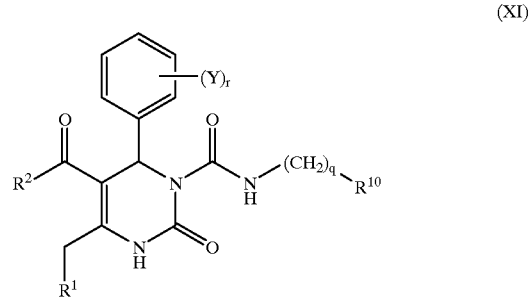

(XI)

comprises treating a dihydropyrimidinone compound of Formula (XII):

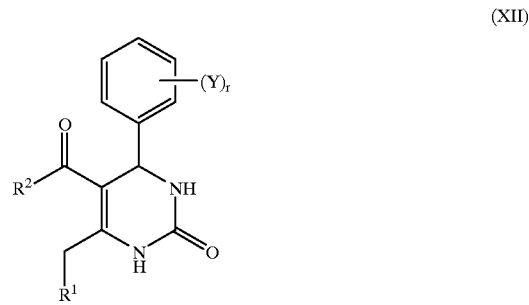

(XII)

with a deprotonation agent; then contacting the treated compound of Formula (II) with at least about one equivalent of carbonyldiimidazole to form an acylimidazolide intermediate; and then contacting with an amine of Formula (XIII):

(XIII)

to form compound (XI); wherein $R^1$ is selected from halogen, $C_{1-4}$ alkyl, $(CH_2)_{0-4}CF_3$, and $C_{1-4}$ alkoxy;

$R^2$ is selected from $C_{1-4}$ alkyl, $(CH_2)_{1-4}CF_3$, $C_{1-4}$ alkoxy, and $O(CH_2)_{1-4}CF_3$;

each Y is independently selected from halogen (preferably fluorine), cyano, $CF_3$, nitro, $C_{1-4}$ alkyl, and $C_{1-4}$ alkoxy;

$R^{10}$ is independently selected from:

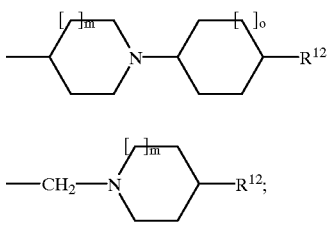

wherein
$R^{12}$ is selected from phenyl; substituted phenyl, wherein the substituents on the phenyl are independently selected from halogen, trifluoromethyl, cyano, nitro, $C_{1-4}$ alkyl, and $C_{1-4}$ alkoxy; and unsubstituted or substituted pyridyl wherein the substituents on the pyridyl are independently selected from halogen, trifluoromethyl, cyano, nitro, $C_{1-4}$ alkyl, and $C_{1-4}$ alkoxy;

m and n are independently integers equal to 0 or 1;
q is an integer from 0 to 3; and
r is an integer from 0 to 3.

Illustrative of the compounds preparable by the above process are (4S)-trans-4-(3,4-difluorophenyl)-3-[1-(4-pyridinyl-2-ylcyclohexyl)-(3R)-pyrrolidin-3-ylcarbamoyl]-6-methyl-2-oxo-1,2,3,4-tetrahydro-pyrimidine-5-carboxylic acid methyl ester of structural formula:

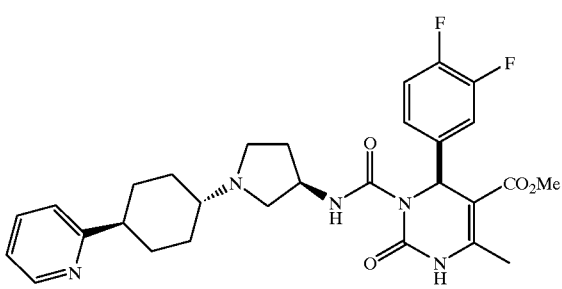

and Compound A.

As used herein, the term "$C_{1-40}$ hydrocarbyl" means a radical attached to the remainder of the molecule by a carbon atom, consisting of carbon atoms and hydrogen atoms and having a total of 1 to 40 carbon atoms. Hydrocarbyl radicals include aliphatic hydrocarbyl groups (e.g., alkyl, alkenyl, or alkynyl), alicyclic hydrocarbyl (e.g., cycloalkyl or cycloalkenyl), aliphatic hydrocarbyl substituted alicyclic hydrocarbyl (e.g., alkyl-substituted cycloalkyl or alkenyl-substituted cycloalkyl), alicyclic hydrocarbyl substituted aliphatic hydrocarbyl (e.g., cycloalkyl-substituted alkyl or cycloalkyl-substituted alkenyl), aromatic hydrocarbyl (e.g., phenyl or naphthyl), aliphatic- and alicyclic-substituted aromatic, aromatic-substituted aliphatic or alicyclic, and the like.

The term "substituted $C_{1-40}$ hydrocarbyl" means a $C_{1-40}$ hydrocarbyl as defined above in which (i) one or more of the hydrogen atoms have been replaced by one or more non-hydrocarbon substituents such as halogen, hydroxy (—OH), mercapto (—SH), oxo (=O), alkoxy (—O-alkyl) primary amino (—$NH_2$), N-alkylamino (—NH-alkyl), N,N-dialkylamino (—N(alkyl)$_2$), carboxamido (—C(=O)$NH_2$), carboxy (—COOH), alkoxycarbonyl (—C(=O)O-alkyl), alkylcarbonyl (C(=O)-alkyl), formyl (—CHO), nitro(—$NO_2$), cyano (—CN), and the like, wherein the alkyl is a linear or branched alkyl; (ii) from one to no more than half (i.e., to no more than 1 in 2, typically to no more than 1 in 3, more typically to no more than 1 in 4, and preferably to no more than 1 in 5) of the carbon atoms (whether aliphatic, alicyclic, or aromatic) have been replaced by one or more heteroatoms such as nitrogen, oxygen, or sulfur; or (iii) a combination of carbon atoms and hydrogen atoms have been replaced in accordance with (i) and (ii).

The term "$C_{1-16}$ alkyl" refers to a $C_1$ to $C_{16}$ linear or branched alkyl group; i.e., the term includes all of the hexadecyl, pentadecyl, tetradecyl, tridecyl, dodecyl, undecyl, decyl, nonyl, octyl, heptyl, hexyl, and pentyl isomers as well as n-, iso-, sec- and t-butyl, n- or isopropyl, ethyl and methyl. Similarly, "$C_{1-10}$ alkyl" refers to a $C_1$ to $C_{10}$ linear or branched alkyl group; i.e., all of the decyl, nonyl, octyl, heptyl, hexyl and pentyl isomers, whether linear or branched, n-, iso-, sec- and t-butyl, n- or isopropyl, ethyl and methyl. "$C_{1-6}$ alkyl" means a $C_1$ to $C_6$ linear or branched alkyl group and refers to all of the hexyl and pentyl isomers, and n-, iso-, sec- and t-butyl, n- or isopropyl, ethyl and methyl. "$C_{1-4}$ alkyl" means a $C_1$ to $C_4$ linear or branched alkyl group and refers to n-, iso-, sec- and t-butyl, n- or isopropyl, ethyl and methyl. "$C_{3-12}$ alkyl" means a $C_3$ to $C_{12}$ linear or branched alkyl group and refers to the propyl to dodecyl isomers inclusive.

"$C_{3-8}$ cycloalkyl" means a cyclic ring of an alkane having three to eight total carbon atoms (i.e., cyclopropyl, cyclobutyl, cyclopentyl, cyclohexyl, cycloheptyl or cyclooctyl). "$C_{3-6}$ cycloalkyl" refers to a cyclic ring selected from cyclopropyl, cyclobutyl, cyclopentyl, and cyclohexyl. "$C_{5-7}$ cycloalkyl" refers to a cyclic ring selected from cyclopentyl, cyclohexyl, and cycloheptyl.

"$C_{1-6}$ alkoxy" refers to an O-alk group wherein alk represents $C_{1-6}$ alkyl as defined above. Similarly, "$C_{1-4}$ alkoxy" refers to a O-Alk group wherein alk represents $C_{1-4}$ alkyl as defined above.

The term "halogen" refers to fluorine, chlorine, bromine, and iodine.

The term "halogen-substituted $C_{1-10}$ alkyl" means a $C_1$ to $C_{10}$ linear or branched alkyl group as defined above substituted with one or more halogens. The term "halogen-substituted $C_{1-6}$ alkyl" means a linear or branched alkyl group as defined above substituted with one or more halogens. Similarly, "halogen-substituted $C_{1-4}$ alkyl" means a $C_1$ to $C_4$ linear or branched alkyl group as defined above substituted with one or more halogens. Representative examples of suitable halo-substituted alkyls include trifluoromethyl, tribromomethyl, 1-fluoroethyl, 2-fluoroethyl, 2,2-difluoroethyl, 2,2,2-trifluoroethyl, 2-bromoethyl, 3,3,3-trifluoro-n-propyl, 3,3,3-trifluoroisopropyl, 1,1,1,3,3,3-hexafluoroisopropyl, and perfluorohexyl The term "halogen-substituted $C_{1-6}$ alkoxy" refers to an O-alk group wherein alk represents $C_{1-6}$ alkyl as defined above substituted with one or more halogens. Representative examples include 2,2,2-trifluoroethyloxy, 2-fluoroethyloxy, trifluoromethoxy, 2-chloroethyloxy, and 3,3,3-trifluoro-n-propyloxy.

The definition of any substituent or variable at a particular location in a molecule is independent of its definitions elsewhere in that molecule. Thus, $N(R^a)2$ wherein $R^a$ is $C_{1-4}$ alkyl represents N(CH$_3$)$_2$, N(CH$_3$)(C$_2$H$_5$), N(C$_2$H$_5$)$_2$, N(C$_2$H$_5$)(C$_3$H$_7$), and so forth.

Where multiple substituents are disclosed or claimed, the substituted compound can be independently substituted by one or more of the disclosed or claimed substituent moieties, singly or plurally.

All ranges given for variables defined to be integers are inclusive ranges; e.g., the term "r is an integer of from 0 to 5" means that r can have any one of the values 0, 1, 2, 3, 4, or 5.

Amines of Formula (III) wherein R is the group represented by Formula (V) wherein R$^{10}$ is of Formula (VI) can be prepared in accordance with Schemes 4–7.

Amines of Formula (III) wherein R is the group represented by Formula (V) wherein R$^{10}$ is of Formula (VII) can be prepared via the methods disclosed in International Publication No. WO 96/14846, published May 23, 1996. See, for example, Schemes 1, 6, and 20 therein.

Amines of Formula (III) wherein R is the group represented by Formula (V) wherein R$^{10}$ is of Formula (VIII) can be prepared in accordance with Schemes 8–12.

Amines of Formula (III) wherein R is the group represented by Formula (V) wherein R$^{10}$ is of Formula (IX) can be prepared in accordance with Schemes 13 and 14.

Amines of Formula (III) wherein R is the group represented by Formula (V) wherein R$^{10}$ is of Formula (X) can be prepared in accordance with Schemes 15–20.

Other methods for preparing amines of Formula (III) wherein R is the group represented by Formula (V) will be readily apparent to the person of ordinary skill in the art in view of the schemes set forth herein and in WO 96/14846.

Scheme 4

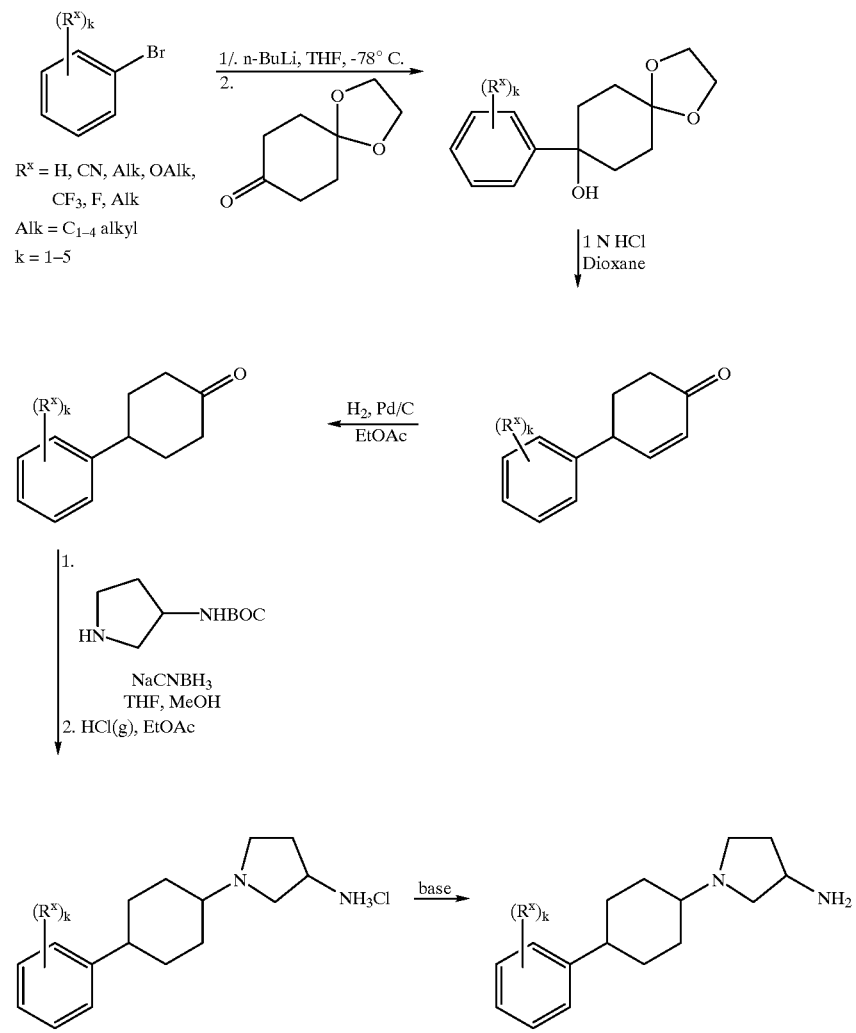

Scheme 5
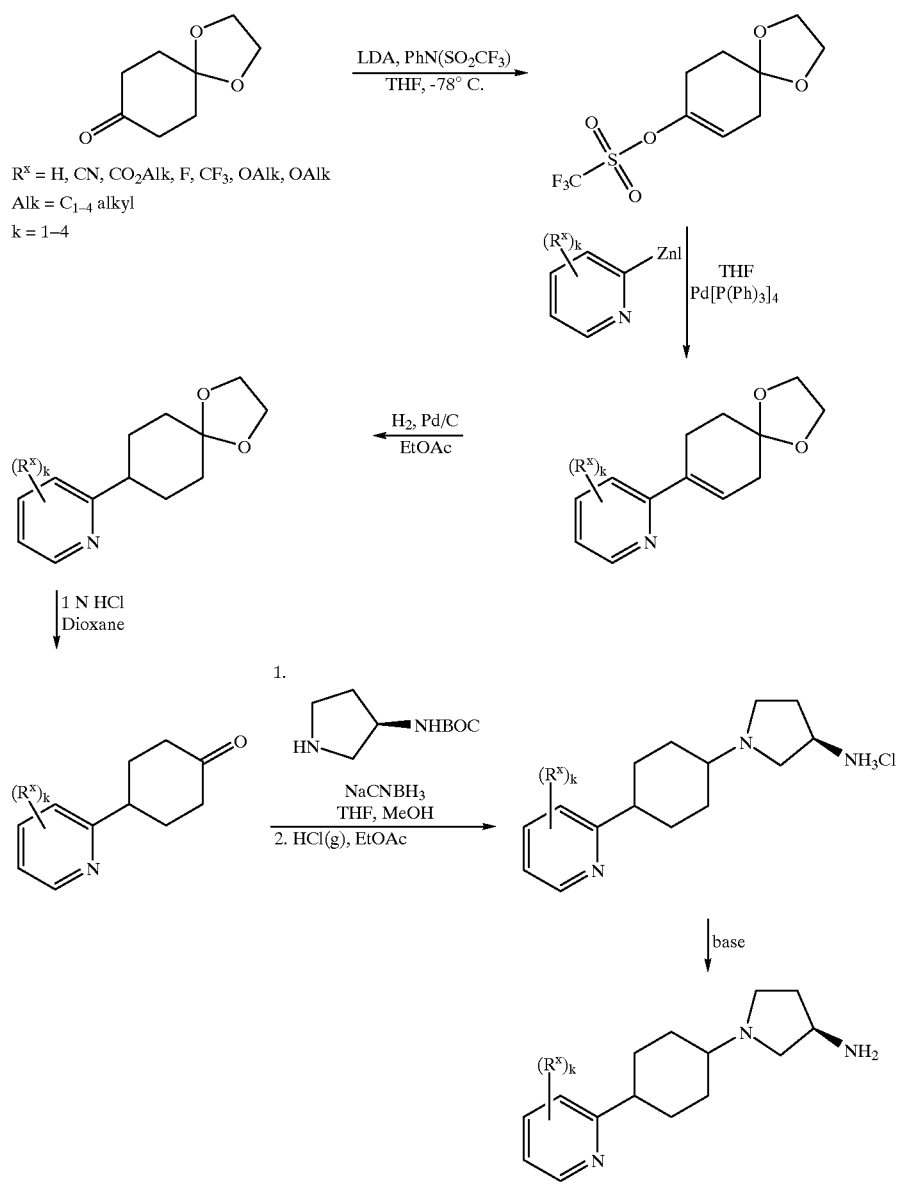
Scheme 6
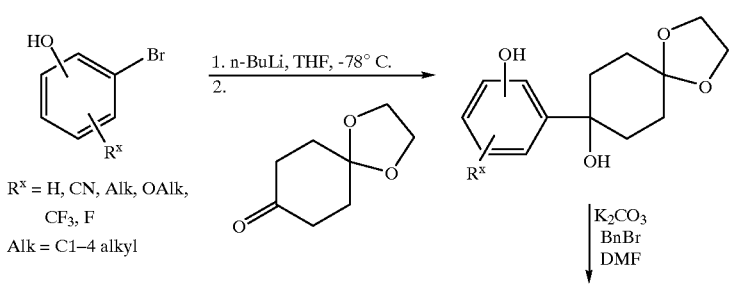

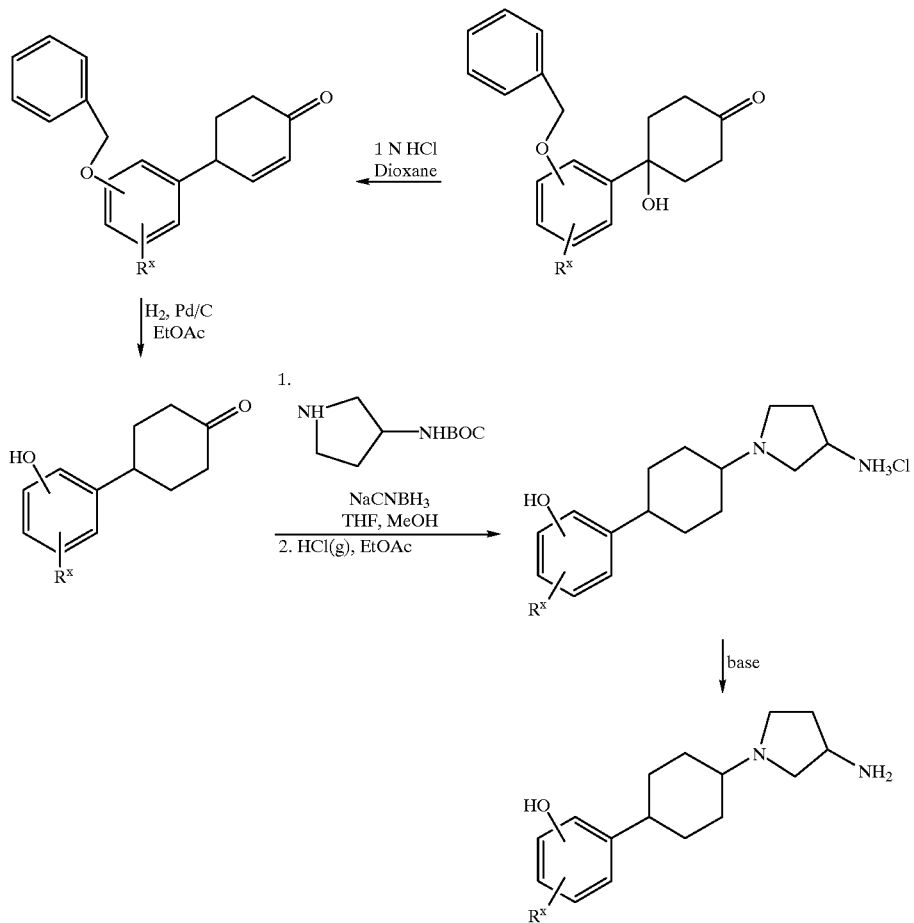
Scheme 7
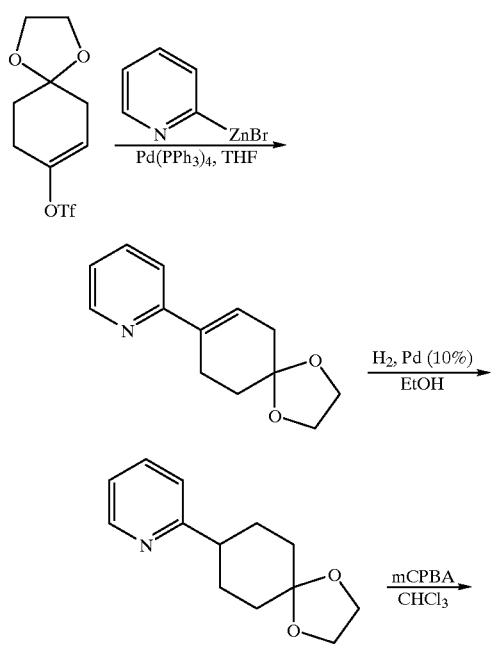
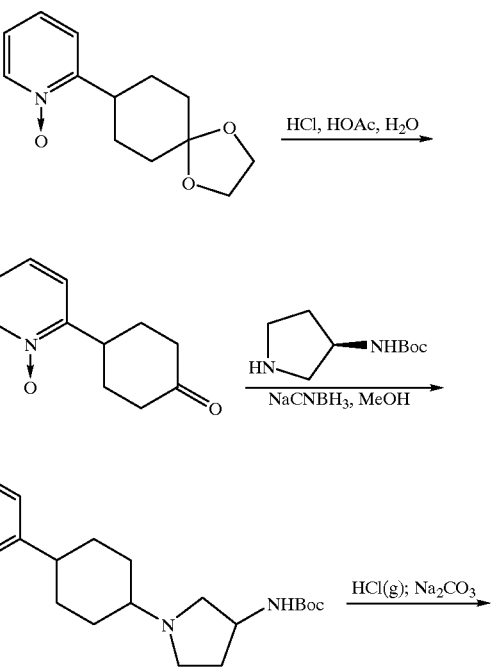

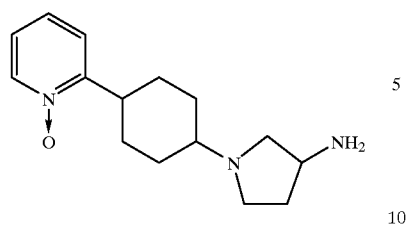
5
Scheme 8
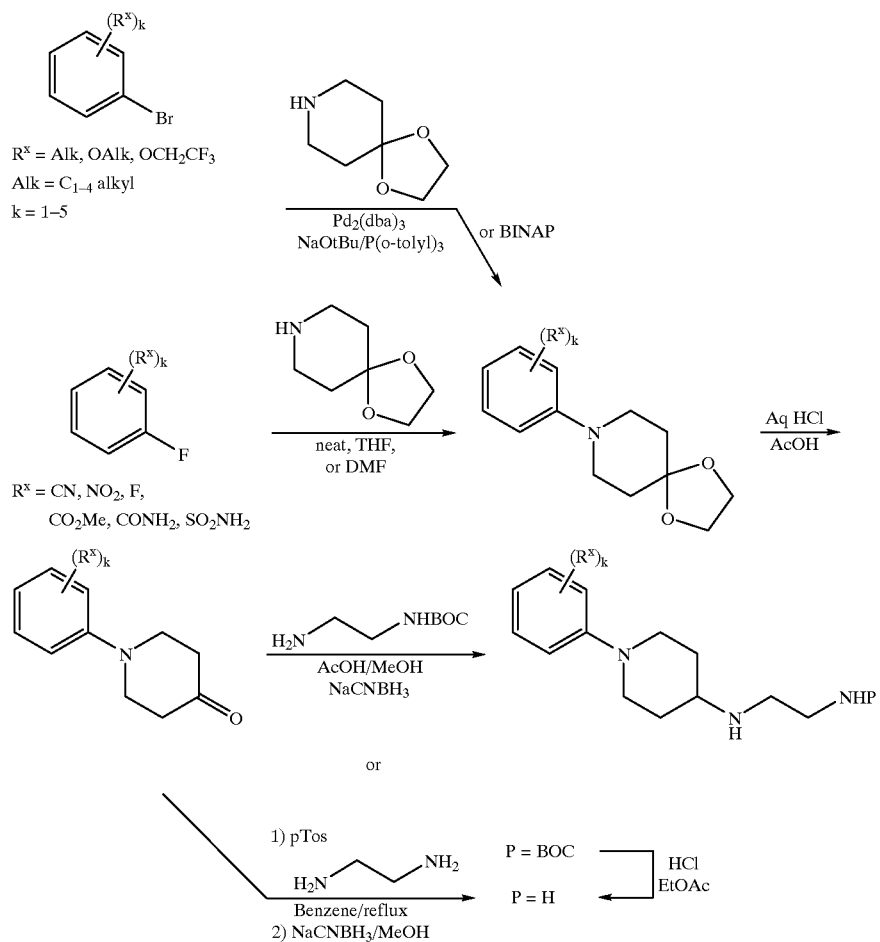
Scheme 9
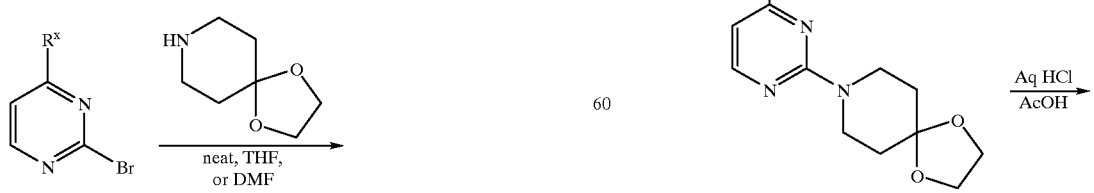

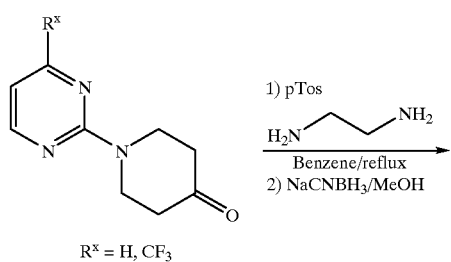
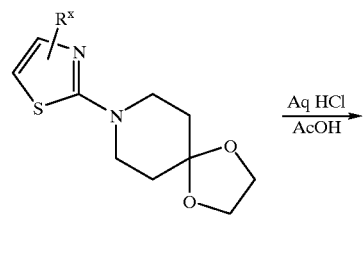
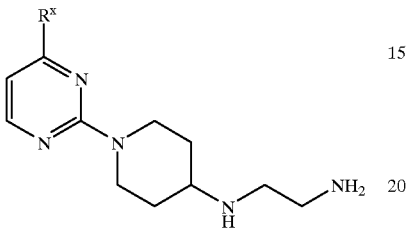
Scheme 10
Scheme 11
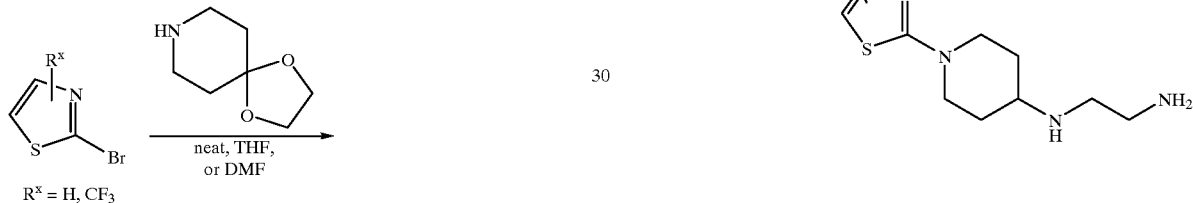
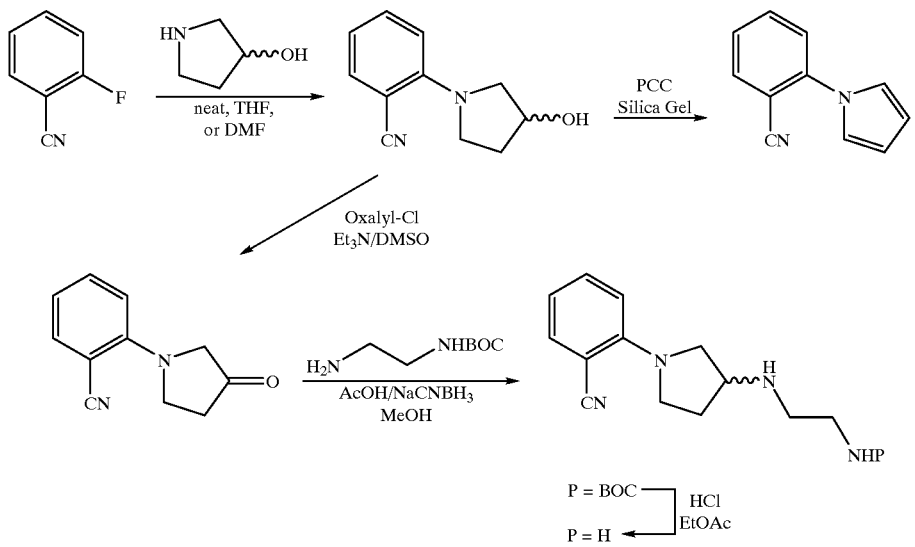

Scheme 12
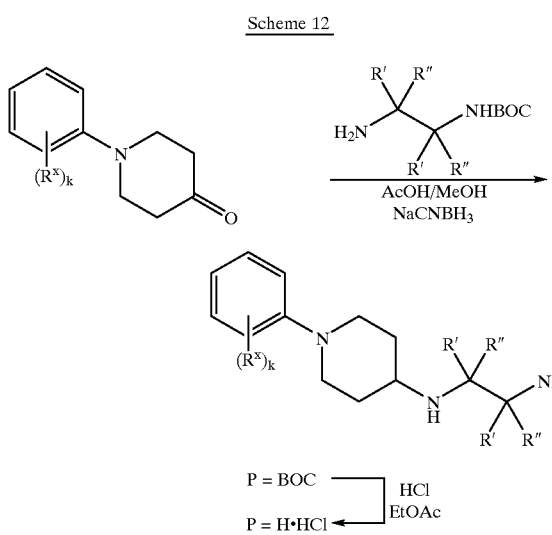
$R^x$ = CN, NO$_2$, Alk, OAlk
Alk = C$_{1-4}$ alkyl
k = 1–5
R', R'' = H, C$_{1-4}$ alkyl, C$_{3-7}$ cycloalkyl
Scheme 13
Synthesis of Cycloalkylaminoethylamines
In general:
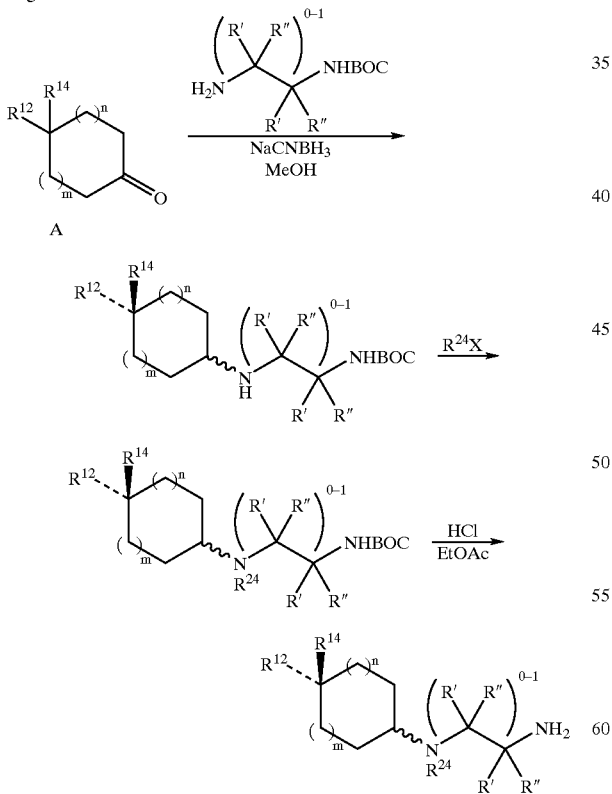
R', R'' = H, C$_{1-8}$ alkyl, C$_{3-8}$ cycloalkyl
For example,
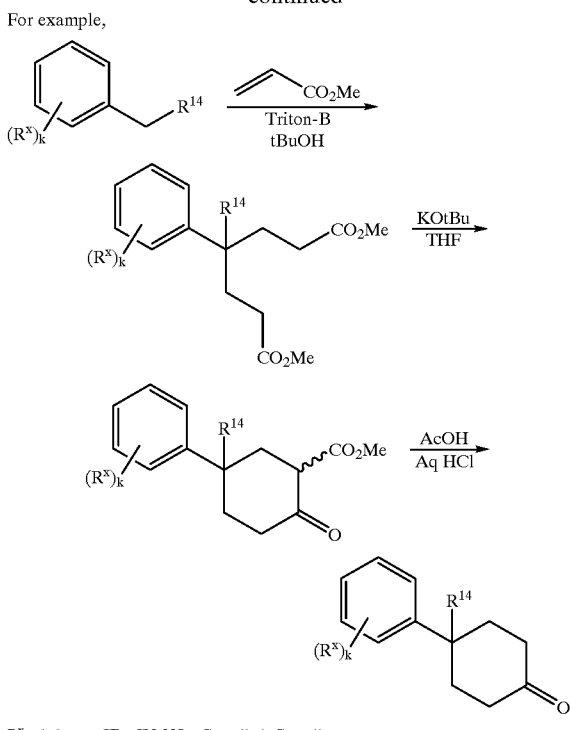
$R^x$ = halogen, CF$_3$, CN, NO$_2$, C$_{1-4}$ alkyl, C$_{1-4}$ alkoxy
k = 1–5
Scheme 14
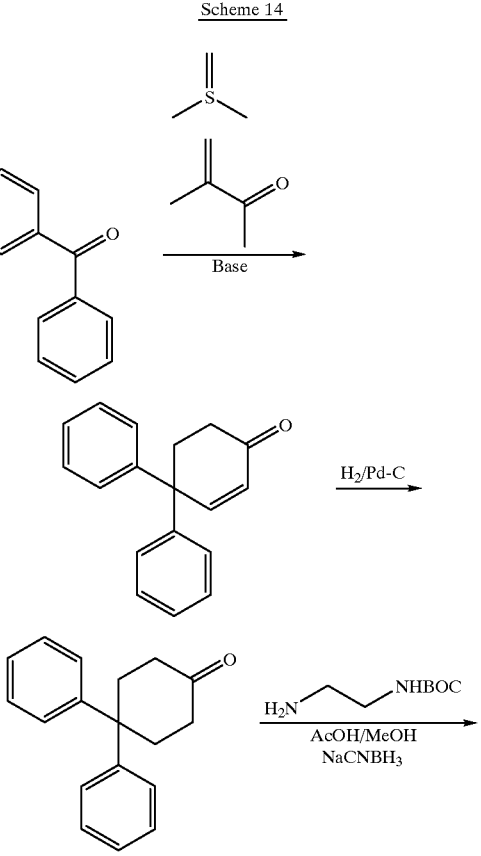

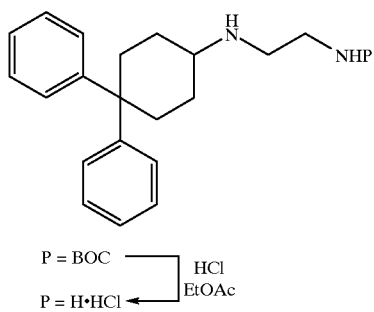
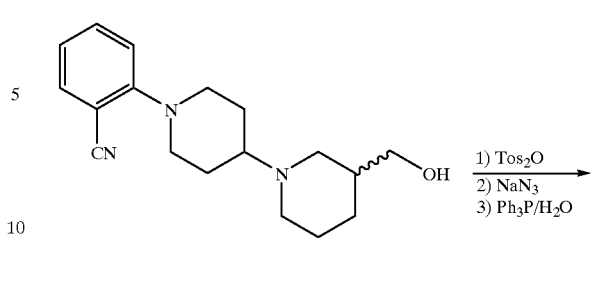
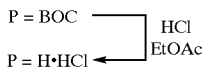
Scheme 15
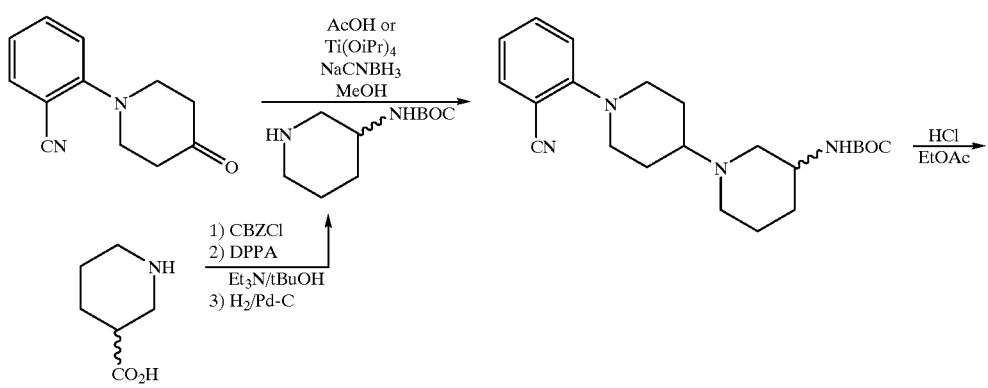
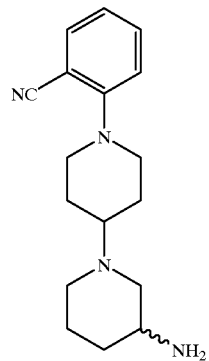
Scheme 16
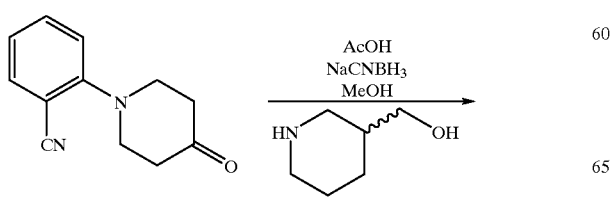
-continued
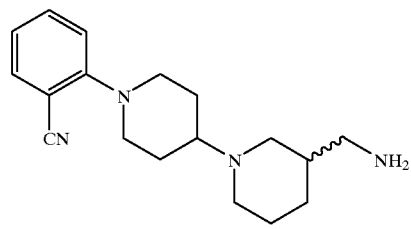

Scheme 17
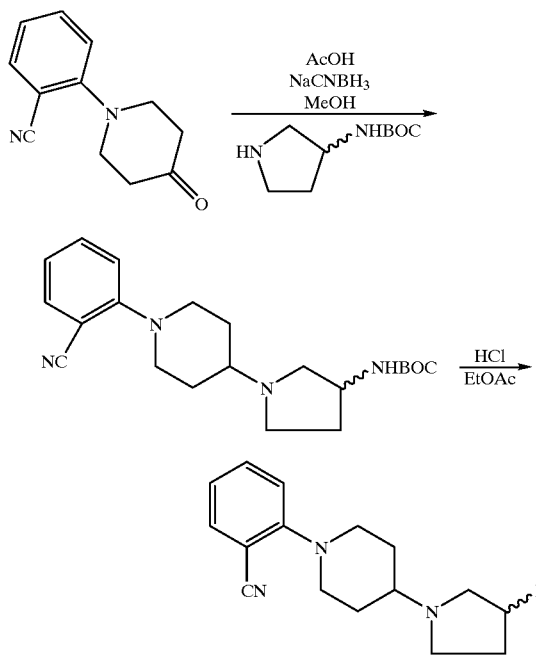
Scheme 18
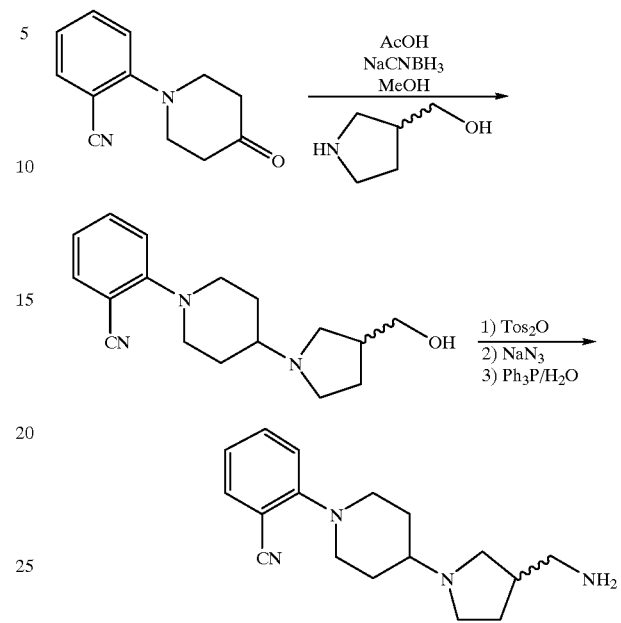
Scheme 19
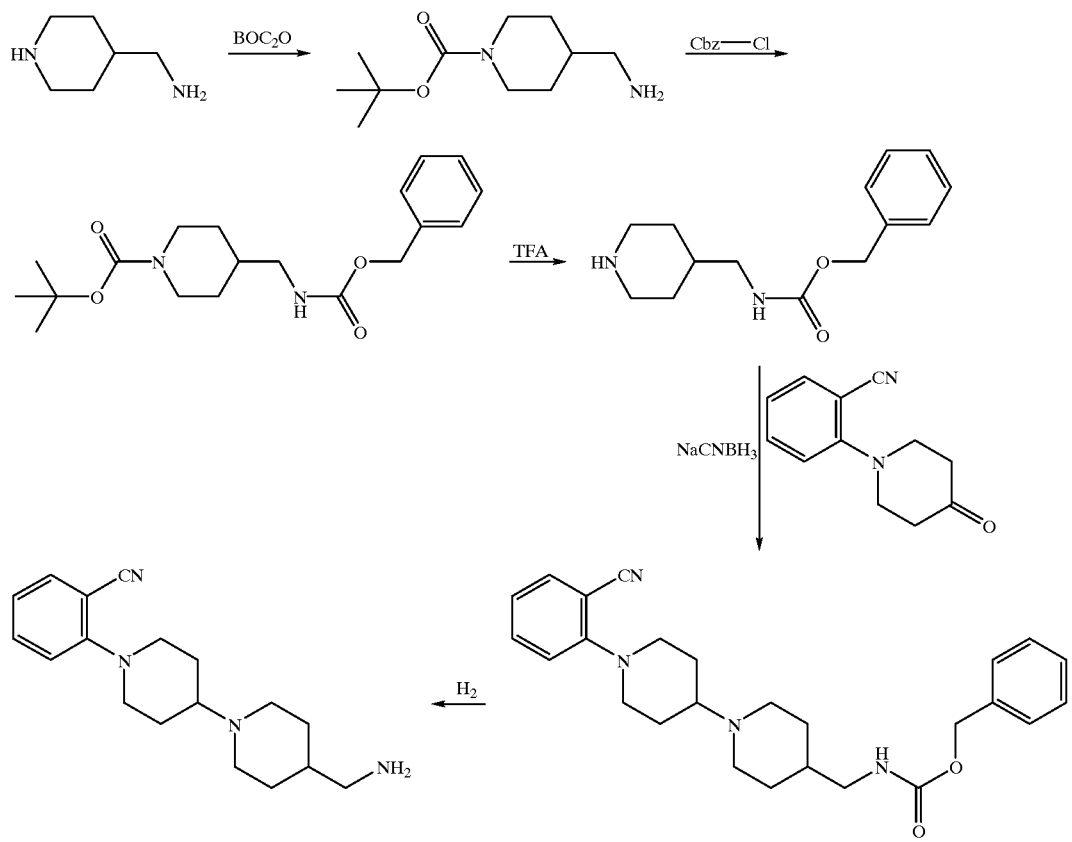

Scheme 20

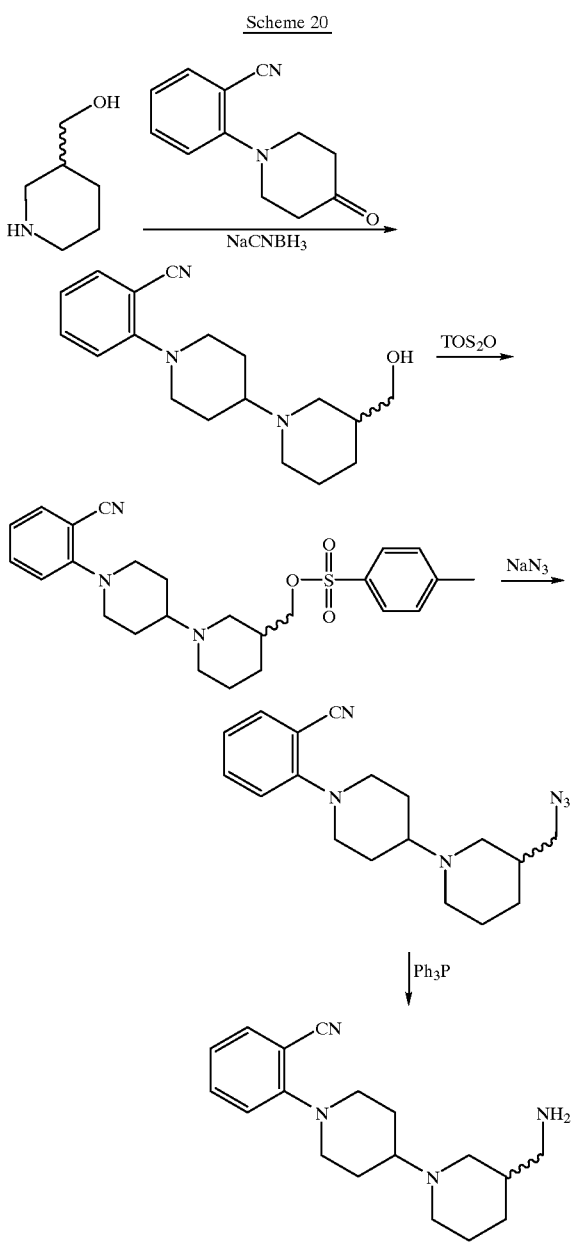

The following examples are provided to further define the invention without, however, limiting the invention to the particulars of these examples.

EXAMPLE 1

1-(3-aminopropyl)-4-(2-pyridyl)pyridinium bromide hydrobromide, (4)

A solution of 2,4'-dipyridyl (820 g, 5.25 mol) and 3-bromopropylamine hydrobromide (1400 g, 6.39 mol) in DMF (5.0 L) was heated to 95° C. for 8 hours. The reaction mixture was cooled to room temperature and methyl tert-butyl ether (3.7 L) was added over 3 hours. The slurry was stirred for 1 hour and filtered. The solid was washed with MTBE/DMF (1:1, 4.2 L) and dried to afford 1-(3-aminopropyl)-4-(2-pyridyl)pyridinium bromide hydrobromide (4) as a tan solid.

EXAMPLE 2

3-[4-(2-pyridyl)-3,4-dehydropiperidin-1-yl]propylamine, (5)

A suspension of 1-(3-aminopropyl)-4-(2-pyridyl)-pyridinium bromide hydrobromide, (4), (1840 g, 4.9 mol) in methanol (18 L) was cooled to 5° C. Sodium borohydride (612 g, 16.2 mol) was added in small portions over 2 hours. Methanol was removed by distillation under reduced pressure. Methyltert-butyl ether (10 L) and 20 wt % aqueous NaOH (20 L) were added. The mixture was stirred for 20 min and the two layers were separated. The aqueous layer was extracted with MTBE (10 L). The combined MTBE extract was concentrated under vacuum to afford 5 as a thick oil, which was dissolved in MeOH (8 L) and used in the next step without further treatment.

EXAMPLE 3

3-[4-(2-pyridyl)piperidin-1-yl]propylamine, (6)

A solution of 3-[4-(2-pyridyl)-3,4-dehydropiperidin-1-yl]propylamine, (5), (900 g, 4.1 mol) in methanol (9 L) was hydrogenated over Pearlman's catalyst (90 g) at 40 psi for 2 hours. The slurry was filtered through Celite® 521, rinsed with methanol (3×300 mL), and the solution was concentrated via rotary evaporation to afford 3-[4-(2-pyridyl)piperidin-1-yl]propylamine, (6), as thick yellow oil.

EXAMPLE 4

3-[4-(2-pyridyl)piperidin-1-yl]-propylamine L-tartrate salt, (7)

A solution of 3-[4-(2-pyridyl)piperidin-1-yl]propylamine, (6), (637.9 g, 3.86 mol) in ethanol (8.5 L) was warmed to 65° C. A solution of L-tartaric acid (637.9 g, 4.25 mol) in ethanol (2.23 L) was added in portions. Approximately 15% of the tartaric acid solution was added and then reaction mixture was aged for 1 hour to afford a thin slurry of crystalline material. The remaining tartaric acid solution was added dropwise. Heating was discontinued and the solution was slowly cooled to ambient temperature overnight. The solids were filtered, rinsed with ethanol (2×1 L) and dried under a stream of nitrogen to afford 3-[4-(2-pyridyl)piperidin-1-yl]propylamine L-tartrate salt, (7), as a pale yellow solid.

EXAMPLE 5

3-[4-(2-pyridyl)piperidin-1-yl]propylamine, (6)

3-[4-(2-pyridyl)piperidin-1-yl]propylamine L-tartrate salt, (7), (1120 g, 3.0 mol) was treated with 5M NaOH (5.7 L, 28.6 mol). The suspension was extracted with isopropyl acetate (3×18 L). The combined extracts were concentrated to afford 3-[4-(2-pyridyl)-piperidin-1-yl]propylamine, (6), as a viscous oil.

EXAMPLE 6

(±)-5-Methoxycarbonyl-6-(3,4-difluorophenyl)-4-methoxymethyl-1,2,3,6-tetrahydro-2-oxopyrimidine, (2)

A solution of methyl 4-methoxyacetoacetate (702 g, 4.8 mol), urea (433 g, 7.2 mol), 3,4-difluorobenzaldehyde (670 g, 4.7 mol), boron trifluoride diethyl etherate(1126 g, 7.9 mol), copper(II) acetate (94 g, 0.52 mol), and acetic acid (36 mL) in THF (7.5 L) was heated to reflux for 8 hours. The reaction mixture was cooled to 20° C. Ethyl acetate (8 L) and 10% citric acid aqueous solution (7.5 kg) was added. The two layers were separated and the aqueous layer was extracted with ethyl acetate (4 L). The combined organic layers were washed with 10% aqueous sodium carbonate (2×5 L) and with 5% brine (1×5 L). The organic layer was concentrated under reduced pressure, with toluene being added continuously and the mixture was concentrated until the level of THF and ethyl acetate was <0.5% volume to toluene, to a final volume was about 2.5 L. The toluene slurry was warmed to 80° C. to dissolve the solids. The solution was cooled slowly to 60° C. and seeded. The slurry was aged at 60° C. for 1 hour and cooled slowly to 20° C. over 4 hours. Hexane (700 mL) was added over 30 minutes. The slurry was aged for 1 hour and filtered. The solid was washed with toluene (1.5 L) and dried to afford (+)-2 as a white solid.

EXAMPLE 7

(+)-(6S)-5-Methoxycarbonyl-6-(3,4-difluorophenyl)-4-methoxymethyl-1,2,3,6-tetrahydro-2-oxopyrimidine, ((+)-2)

A 100-L reaction vessel was charged with 50 mM Tris buffer (Tris HCl (77.4 g) and Tris Base (196.7 g) in deionized water (42.3 L)), 12.0 L of subtilisin (PURAFECT® 4000 L, available from Genencor International), acetonitrile (5.7 L), and (±)-5-methoxycarbonyl-6-(3,4-difluorophenyl)-4-methoxymethyl-1,2,3,6-tetrahydro-2-oxopyrimidine, (2), (120 g, 0.38 mol) and the mixture was allowed to react at 37° C., pH 8.3 for 9 days. The reaction mixture was extracted with toluene (10 L). The aqueous layer was separated and washed with toluene (5 L). The combined organic extracts were washed with brine (10 L). The organic layer was concentrated by rotary evaporation, filtered, then adjusted to 400 mL volume with toluene. The (+)-2 was crystallized by adding heptane (80 mL), followed by seeding. The mixture was stirred for 1 hr, then heptane (520 mL) was added over 8 hrs. The crystals were filtered, washed with 3:2 heptane-toluene (150 mL), then dried under high vacuum to yield (+)-(6S)-5-methoxycarbonyl-6-(3,4-difluorophenyl)-4-methoxymethyl-1,2,3,6-tetrahydro-2-oxopyrimidine, ((+)-2) as a white solid.

EXAMPLE 8

(+)-5-Methoxycarbonyl-6-(3,4-difluorophenyl)-4-methoxycarbonyl-1-{N-[3-(4-(2-pyridyl)piperidin-1-yl)propyl]}carboxamido-1,2,3,6-tetrahydro-2-oxopyrimidine, (3)

A solution of (+)-(6S)-5-methoxycarbonyl-6-(3,4-difluorophenyl)-4-methoxymethyl-1,2,3,6-tetrahydro-2-oxopyrimidine, ((+)-2), (100 g, 0.32 mol) in THF (1 L) was cooled to -65° C. A solution of LDA (2M in heptane/THF/ethylbenzene, 184 mL, 0.36 mol) was added in a thin stream. The resulting clear solution was aged for 15 min., then carbonyl diimidazole (62.3 g, 0.38 mol) was added as a solid in one portion. The resulting slurry was aged for 15 min at ca. −60° C., then warmed to 20° C. and aged for 1 hour. The thin yellow suspension was cooled to −60° C. A solution of 3-[4-(2-pyridyl)piperidin-1-yl]propylamine, (6), (100 g, 0.45 mol) in IPAc was added. The reaction mixture was slowly warmed to 20° C. After 1 hour at 20° C., the reaction was quenched with H₂O (1.5 L) and IPAc (1.5 L). The layers were separated. The organic layer was washed with H₂O (2×1.5 L). The combined aqueous layers were washed with IPAc (1×0.5 L). The combined organic layers were extracted with 2N HCl (1×1 L and 1×0.5 L). The combined HCl extracts were neutralized by the cautious addition of solid NaHCO₃ (450 g). IPAc (1 L) and H₂O (1 L) were added to the bicarbonate layer. The layers were separated. The aqueous bicarbonate layer was washed with IPAc (1×1 L). The combined product containing IPAc layers were washed with H₂O (2×1 L). The organic layer was concentrated to afford (+)-5-methoxycarbonyl-6-(3,4-difluorophenyl)-4-methoxycarbonyl-1-{N-[3-(4-(2-pyridyl)piperidin-1-yl)propyl]}carboxamido-1,2,3,6-tetrahydro-2-oxopyrimidine, (3), as a thick oil.

EXAMPLE 9

Crystallization of (+)-5-Methoxycarbonyl-6-(3,4-difluorophenyl)-4-methoxycarbonyl-1-{N-[3-(4-(2-pyridyl)piperidin-1-yl)propyl]}carboxamido-1,2,3,6-tetrahydro-2-oxopyrimidine L-tartrate salt, (1)

Crude (+)-5-methoxycarbonyl-6-(3,4-difluorophenyl)-4-methoxycarbonyl-1-{N-[3-(4-(2-pyridyl)piperidin-1-yl)propyl]}carboxamido-1,2,3,6-tetrahydro-2-oxopyrimidine, (3), (150 g) was dissolved in 2-propanol (1.27 L) at 50° C. Approximately 50 mL of a solution of L-tartaric acid (40.7 g) in EtOH (175 mL) was added to the solution of 3 at 50° C. The solution was aged for 1 hour for crystals to develop, then the remaining L-tartaric acid was added over 0.5 hour. The suspension of 1 was cooled to 20° C. After overnight age, the suspension was cooled to 0° C. and filtered. The cake was rinsed with 2-propanol (2×150 mL) and dried by pulling N₂ through the cake to afford (+)-5-methoxycarbonyl-6-(3,4-difluorophenyl)-4-methoxycarbonyl-1-{N-[3-(4-(2-pyridyl)piperidin-1-yl)propyl]}carboxamido-1,2,3,6-tetrahydro-2-oxopyrimidine L-tartrate salt, (1), as a white, free-flowing solid. This crystalline form of (1), designated as Type A, was determined to be an isopropanol solvate.

$^1$H NMR (DMSO-d$_6$): 9.95 (s, 1H), 8.81 (t, J=5.6, 1H), 8.49 (m, 1H), 7.71 (td, J=7.8, 1.8, 1H), 7.41 (dt, J=10.5, 8.6, 1H), 7.28 (d, J=7.8, 1H), 7.20 (m, 2H), 7.08 (m, 1H), 6.56 (s, 1H), 4.63 (d, J=13.1, 1H), 4.43 (d, J=13.1, 1H), 4.08 (s, 2H), 3.67 (s, 3H), 3.29 (s, 3H), 3.25 (m, 4H), 2.79 (m, 1H), 2.71 (t, J=7.3, 2H), 2.52 (m, 2H), 1.89 (m, 4H), 1.78 (m, 2H).

$^{13}$C NMR (DMSO-d$_6$): 173.8, 164.4, 163.4, 152.9, 152.2, 149.2 (dd, J=246.5, 24.7), 149.0 (dd, J=246.5, 24.2), 148.9, 146.8, 138.0 (t, J=4.5), 136.7, 123.0 (dd, J=6.7, 3.5), 121.7, 121.3, 117.9 (d, J=17.2), 115.3 (d, J=17.6), 103.1, 71.8, 66.7, 58.2, 54.4, 52.3, 51.8, 51.7, 41.9, 38.1, 29.7, 24.9.

Type A is characterized by a differential scanning calorimetry (DSC) curve, at a heating rate of 10° C./min in an open cup under flowing nitrogen, exhibiting a relatively broad endotherm with an extrapolated onset temperature of about 56° C., a peak temperature of about 90° C. and an associated heat of about 23 J/gm followed by an endotherm with an extrapolated onset temperature of about 108° C., a peak temperature of about 115° C. and an associated heat of about 13 J/gm followed by an endotherm with an extrapolated onset temperature of about 145° C., a peak temperature of about 148° C. and an associated heat of about 57 J/gm. The two low temperature endotherms are due to the loss of isopropanol and the high temperature endotherm is due to melting with decomposition of the remaining unsolvated phase (Type B).

The X-ray powder diffraction pattern of Type A is characterized by d-spacings of 14.91, 8.32, 6.88, 5.41, 4.74, 4.29, 4.04, 3.86, 3.75 and 3.59 Å.

A second crystalline form of (1), designated as Type B which is unsolvated material, was prepared either by swishing Type A in ethanol followed by filtration and subsequent drying, or by heating Type A to ~115° C. for about 20 minutes.

More specifically, Compound A tartrate salt Type A (2-propanol solvate) (10 g) was suspended in ethanol (50 mL) at 0° C. in a flask fitted with a mechanical stirrer, addition funnel, and thermocouple under a $N_2$ atmosphere. The solution was aged for 2 hours and then filtered. The cake was rinsed with ethanol (2×5 mL) and dried by pulling $N_2$ through the cake to afford Compound A tartrate salt Type B as a white, free-flowing solid. The $^1H$ and $^{13}C$ NMR spectra for Type B are identical to the spectra for Type A shown above.

Type B is characterized by a differential scanning calorimetry (DSC) curve, at a heating rate of 10° C./min in an open cup under flowing nitrogen, exhibiting an endotherm with an extrapolated onset temperature of about 144° C., a peak temperature of about 148° C. and an associated heat of about 65 J/gm. The endotherm is due to melting with decomposition.

The X-ray powder diffraction pattern of Type B is characterized by d-spacings of 13.29, 7.82, 6.63, 6.20, 5.36, 5.01, 4.59, 4.35, 4.05, 3.73 and 3.60 Å.

EXAMPLE 10

As a specific embodiment of an oral composition, 100 mg of the compound of Example 9 (Type B) is formulated with sufficient finely divided lactose to provide a total amount of 580 to 590 mg to fill a size O hard gel capsule.

EXAMPLE 11

Synthesis of racemic DHP methyl ester, i.e., (±)-5-Methoxycarbonyl-6-(3,4-difluorophenyl)-4-methoxymethyl-1,2,3,6-tetrahydro-2-oxopyrimidine, (2)

A solution of methyl 4-methoxyacetoacetate (702 g, 4.8 mol), urea (433 g, 7.2 mol), 3, 4-difluorobenzaldehyde (670 g, 4.7 mol), boron trifluoride diethyl etherate(1126 g, 7.9 mol), copper(II) acetate (94 g, 0.52 mol), and acetic acid (36 mL) in THF (7.5 L) was heated to reflux for 8 hours. The reaction mixture was cooled to 20° C. Ethyl acetate (8 L) and 10% citric acid aqueous solution (7.5 kg) was added. The two layers were separated and the aqueous layer was extracted with ethyl acetate (4 L). The combined organic layers were washed with 10% aqueous sodium carbonate (2×5 L) and with 5% brine (1×5 L). The organic layer was concentrated under reduced pressure, with toluene being added continuously and the mixture was concentrated until the level of THF and ethyl acetate was <0.5% volume to toluene, to a final volume was about 2.5 L. The toluene slurry was warmed to 80° C. to dissolve the solids. The solution was cooled slowly to 60° C. and seeded. The slurry was aged at 60° C. for 1 hour and cooled slowly to 20° C. over 4 hours. Hexane (700 mL) was added over 30 minutes. The slurry was aged for 1 hour and filtered. The solid was washed with toluene (1.5 L) and dried to afford racemic DHP methyl ester, (±)-2, as a white solid

EXAMPLE 12
Enzymatic Screening

An amount of 125 mg of racemic DHP methyl ester ((±)-2) was added to 100 ml of Tris buffer (50 mM, pH 7.5) and 500 mg of xanthan gum. The mixture was blended at high speed in a commercial blender for 2 minutes. The emulsion was dispensed (10 ml) into 250-ml Erlenmeyer flasks. To each flask, an enzyme (lipase, esterase, or protease) to be evaluated was added. The flasks were incubated at 30° C. Samples (1 ml) were taken after 24 and 48 hours of incubation and were diluted with 1 ml of acetonitrile, centrifuged, and filtered. HPLC analyses (method described below) revealed the presence of dihydropyrimidinone acid (8) in the flasks to which 100 mg of Proteinase K or 25 mg of Subtilisin were added. SFC analyses (described below) indicated that the acid (8) produced had an enantiomeric excess greater than 95%, and that an enrichment in one of the ester enantiomers had taken place.

Reverse phase HPLC was used to quantitate the ester (2) and acid (8) in the reaction mixture. The sample was prepared by mixing 1 ml of the reaction mixture with 1 ml acetonitrile. The mixture was filtered through a 0.3-μm filter and 10 μl was injected. The column is an Inertsil 5 ODS (4.6 mm×25 cm). A gradient elution at 1 ml/min from 25% to 40% acetonitrile in water, each with 0.1% trifluoroacetic acid, is used to detect at 280 nm. The change in chiral purity of the ester (2) with time was monitored using an SFC assay. The samples were prepared by evaporating 0.1 ml reaction mixture under a stream of nitrogen, dissolving the residue in 1 ml methanol, and filtering through a 0.3-μm filter. The column used is a Chiralcel OD-H (4.6 mm×25 cm). An isocratic elution at 2 ml/min, 35° C., and 290 bar of 6% methanol in $CO_2$ is used to detect at 280 nm.

EXAMPLE 13
Bioresolution of Racemic Ester using Proteinase K

A 50 mM Tris buffer was prepared by dissolving 2.46 g Tris HCl and 2.96 g Tris Base in 800 ml deionized water. This buffer, along with 4 g xanthan gum and 0.8 g ester (±)-2, was added to a commercial blender used to emulsify the mixture by blending for 2 min. The resulting emulsion and 8 g Proteinase K (Sigma, 14 U/mg) were added to a 1-L reaction vessel and allowed to react at 37° C., pH 8.0, and an agitation rate of 300 RPM for 6 days. After 6 days, 89% of the (R)-ester had been hydrolyzed by the Proteinase K to the acid form, leaving (S)-ester of an 80% enantiomeric excess (e.e.). The reaction was diluted with equal volume of acetonitrile to precipitate the xanthan gum, which was removed by filtration through cotton. The filtrate was evaporated to half volume by rotary evaporation, and the resulting aqueous liquid was extracted three times with ethyl acetate. The organic layer was dried over anhydrous $MgSO_4$ and concentrated by rotary evaporation to yield a residue, which was purified by silica gel flash chromatography, eluting with 60–80% ethyl acetate in hexane to yield 0.29 g (72% of theoretical yield) of (S)-DHP methyl ester ((+)-S -2) (80% e.e.) Pure (R)-DHP acid ((−)-R-8) was also isolated. The aqueous layer was acidified with concentrated HCl, saturated with NaCl, and extracted once with ethyl acetate. The organic layer was dried, concentrated, and the residue was purified by crystallization from methanol. Two crops yielded 0.14 g of (R)-DHP acid ((−)-R-8).

EXAMPLE 14
Bioresolution of 3 g/l Racemic Ester using Subtilisin

A 50 mM Tris buffer was prepared by dissolving 5.2 g Tris HCl and 37.2 g Tris Base in 6.8 L deionized water. This buffer, along with 2.0 L of the Subtilisin, PURAFECT® 4000 L, 1.2 L of acetonitrile, and 30 g ester (±)-2 was added to a 14-L reaction vessel and the mixture was allowed to react at 45° C., pH 8.5, and an agitation rate of 125 RPM for 16 days. An additional 400 ml of Subtilisin was passed through a tangential flow filtration module (10 kDalton mass exclusion, 2.5 $ft^2$ area), exchanging half of the volume with Tris buffer of the same makeup as that used in the reaction. This filtered enzyme and 50 ml acetonitrile were added to the reaction vessel after the first 13 days of the bioresolution. The concentrations of ester (2) and acid (8) and chiral purity of ester in the reaction were assayed with HPLC and SF-HPLC as described above. After 16 days, 98% of the (R)-ester had been hydrolyzed by the Subtilisin to the acid form, leaving (S)-ester of a 96% e.e. The aqueous mixture was extracted with 3 L+1 L toluene. The combined organic layers were washed with 2 L brine, filtered through cotton, then rotary evaporated to ca. 50 ml volume. Ca. 10 ml of hexane was added until cloudiness persisted, warmed to clear the solution, then allowed to age overnight to crystallize out the ester. The mother liquor was poured out, then the crystals were washed twice with 2–3 ml toluene. The crystals were dried overnight under high vacuum to afford 9.1 g (60% of theoretical yield) of (S)-DHP methyl ester, (+)-S -2 (99% e.e.). The aqueous layer after the toluene extraction was acidified with concentrated HCl and then saturated with NaCl. The aqueous layer was extracted once with 4 L ethyl acetate, and the mixture was allowed to settle. The lower clear aqueous layer was drained, and the upper organic layer, which was an emulsion with particulates, was swirled with solka floc and filtered through a glass sintered funnel. The now clear organic layer of the filtrate was dried over anhydrous $MgSO_4$ and concentrated by rotary evaporation. The residue was dissolved in 150 ml methanol with heating, seeded with (R)-DHP acid crystals, and allowed to stir overnight at room temperature. The crystals were filtered and washed with methanol to afford pure acid. After the second crop, a total of 8.6 g (60% of theoretical yield, >99% A, >99% e.e.) of (R)-DHP acid, (–)-R-8, was obtained as a fine white solid.

EXAMPLE 15

Bioresolution of 2 g/l Racemic Ester using Subtilisin (10-L Scale)

A 50 mM Tris buffer was prepared by dissolving 12.9 g Tris HCl and 32.8 g Tris Base in 7.05 L deionized water. This buffer, along with 2.0 L of the Subtilisin, PURAFECT® 4000 L, 0.95 L of acetonitrile, and 20 g ester, (±)-2, was added to a 14-L reaction vessel and the mixture was allowed to react at 37° C., pH 8.3, and an agitation rate of 125 RPM for 10 days. The concentrations of ester (2) and acid (8) and chiral purity of ester in the reaction were assayed with HPLC and SF-HPLC as described above. After 10 days, >99% of the (R)-ester had been hydrolyzed by the Subtilisin to the acid form, leaving (S)-ester of a 98% e.e. Two 10-L reactions were combined in a 50-L extractor and were extracted with 4 L+2 L toluene. The combined organic layer was washed with 3.5 L brine and then concentrated by rotary evaporation. The residue was dissolved in toluene, filtered through a glass sintered funnel, and then brought up to 150 ml total volume in a 1-L 3-neck flask equipped with an overhead stirrer and an addition funnel. Heptane (55 ml) was added over 30 min, and then seed crystals of (S)-DHP methyl ester were added. After 1.5 hr stirring to generate the seed bed, 195 ml more heptane were added over 4 hr. The mixture was allowed to stir overnight and then the crystals were filtered and washed with 50 ml heptane:toluene (2:1). The crystals were dried under a vacuum to yield 18.5 g (46% recovery) of (S)-DHP methyl ester, (+)-S -2 (95 area %, 99.5% e.e.).

EXAMPLE 16

Alternative Purification Conditions

The (S)-DHP methyl ester (+)-S-2 generated in Example 10 could be isolated from the aqueous reaction mixture by extraction with various organic solvents such as ethyl acetate, toluene, and dichloromethane. After concentration of the extract, the ester could be purified by silica gel chromatography or by crystallization. The (S)-DHP methyl ester, (+)-S-2, could also be isolated from the aqueous mixture by passing the reaction mixture through a resin column (Supelco SP-207 resin), washing the column with water, and eluting the retained ester off the resin with methanol.

EXAMPLE 17

Bioresolution of 2 g/l Racemic Ester using Subtilisin (1500-L Scale)

A 50 mM Tris buffer was prepared by dissolving 1.3 kg Tris HCl and 5.5 kg Tris Base in 1060 L deionized water. This buffer, along with 300 L of the Subtilisin, PURAFECT® 4000 L, 140 L of acetonitrile, and 3.2 kg ester (±)-2 was added to a 1900-L reaction vessel and the mixture was allowed to react at 37° C., pH 8.5, and an agitation rate of 50 RPM for 10 days. The concentrations of ester (2) and acid (8) and chiral purity of ester (2) in the reaction were assayed with HPLC and SF-HPLC as described above. After 10 days, 98% of the (R)-ester had been hydrolyzed by the Subtilisin to the acid form, leaving (S)-ester of a 97% e.e. The reaction mixture was extracted with 182 kg+133 kg toluene. The combined organic layer was washed with 35 gal brine and then vacuum concentrated, first in a 100-gal tank and then in a 50-L round-bottom flask, to a volume of 3 L. An additional 4 L toluene was charged to the mixture, which was then evaporated down to 3 L. This was repeated a second time to remove the water azeotropically. The concentrated solution was filtered through a sintered funnel into a 50-L round-bottom flask and brought up to 11 L total volume with fresh toluene. Heptane (95 ml) was added to 500 ml of the concentrated toluene solution over 20 min, and then seed crystals of (S)-DHP methyl ester, (+)-S-2, were added. After 1 hr stirring to generate the seed bed, 677 ml more heptane were added over 6.5 hr. After stirring 1 hr more, the crystals were filtered using a sintered funnel and washed with 200 ml heptane:toluene (3:2). The crystals were dried under a vacuum to yield 58 g ester. Heptane (2 L) was added to the remaining 10.5 L of the concentrated toluene solution over 20 min, and then the 58 g ester were added as seed crystals. After 1 hr stirring to generate the seed bed, 13.8 L more heptane were added over 8 hr. The mixture was stirred overnight and the crystals were filtered using a Buchner funnel and washed with 5.7 L heptane:toluene (3:2). The crystals were dried with nitrogen for 8 hr and in an oven for 4 days at 30° C. under high vacuum and with a nitrogen sweep. This afforded 1.28 kg (40% recovery) of (S)-DHP methyl ester, (+)-S -2 (98% e.e.).

EXAMPLE 18

Synthesis of Compound A from DHP methyl ester: i.e., (+)-5-methoxycarbonyl-6-(3,4-difluorophenyl)-4-methoxycarbonyl-1-{N-[3-(4-(2-pyridyl)piperidin-1-yl)propyl]}carboxamido-1,2,3,6-tetrahydro-2-oxopyrimidine L-tartrate salt (1)

A solution of (S)-DHP methyl ester, (+)-S -2(100 g, 0.32 mol) in THF (1 L) was cooled to −65° C. A solution of LDA (2M in heptane/THF/ethylbenzene, 184 mL, 0.36 mol) was added in a thin stream. The resulting clear solution was aged for 15 min., then carbonyl diimidazole (62.3 g, 0.38 mol) was added as a solid in one portion. The resulting slurry was aged for 15 min at ca. −60° C., then warmed to 20° C. and aged for 1 hour. The thin yellow suspension was cooled to −60° C. A solution of 3-[4-(2-pyridyl)piperidin-1-yl]

propylamine (100 g, 0.45 mol) in IPAc was added. The reaction mixture was slowly warmed to 20° C. After 1 hour at 20° C., the reaction was quenched with H$_2$O (1.5 L) and IPAc (1.5 L). The layers were separated. The organic layer was washed with H$_2$O (2×1.5 L). The combined aqueous layers were washed with IPAc (1×0.5 L). The combined organic layers were extracted with 2N HCl (1×1 L and 1×0.5 L). The combined HCl extracts were neutralized by the cautious addition of solid NaHCO$_3$ (450 g). IPAc (1 L) and H$_2$O (1 L) were added to the bicarbonate layer. The layers were separated. The aqueous bicarbonate layer was washed with IPAc (1×1 L). The combined product containing IPAc layers were washed with H$_2$O (2×1 L). The organic layer was concentrated to afford (+)-5-methoxycarbonyl-6-(3,4-difluorophenyl)-4-methoxycarbonyl-1-{N-[3-(4-(2-pyridyl)piperidin-1-yl)propyl]}carboxamido-1,2,3,6-tetrahydro-2-oxopyrimidine (3) as a thick oil. Crude (+)-5-methoxycarbonyl-6-(3,4-difluorophenyl)-4-methoxycarbonyl-1-{N-[3-(4-(2-pyridyl)piperidin-1-yl)propyl]}carboxamido-1,2,3,6-tetrahydro-2-oxopyrimidine, 3 (150 g) was dissolved in 2-propanol (1.27 L) at 50° C. Approximately 50 mL of a solution of L-tartaric acid (40.7 g) in EtOH (175 mL) was added to the solution at 50° C. The solution was aged for 1 hour for crystals to develop, then the remaining L-tartaric acid was added over 0.5 hour. The suspension was cooled to 20° C. After overnight age, the suspension was cooled to 0° C. and filtered. The cake was rinsed with 2-propanol (2×150 mL) and dried by pulling N$_2$ through the cake to afford (+)-5-methoxycarbonyl-6-(3,4-difluorophenyl)-4-methoxycarbonyl-1-{N-[3-(4-(2-pyridyl)piperidin-1-yl)propyl]}carboxamido-1,2,3,6-tetrahydro-2-oxopyrimidine L-tartrate salt (1) as a white, free-flowing solid. This crystalline form of (1), designated as Type A, was determined to be an isopropanol solvate.

$^1$H NMR (DMSO-d$_6$): 9.95 (s, 1H), 8.81 (t, J=5.6, 1H), 8.49 (m, 1H), 7.71 (td, J=7.8, 1.8, 1H), 7.41 (dt, J=10.5, 8.6, 1H), 7.28 (d, J=7.8, 1H), 7.20 (m, 2H), 7.08 (m, 1H), 6.56 (s, 1H), 4.63 (d, J=13.1, 1H), 4.43 (d, J=13.1, 1H), 4.08 (s, 2H), 3.67 (s, 3H), 3.29 (s, 3H), 3.25 (m, 4H), 2.79 (m, 1H), 2.71 (t, J=7.3, 2H), 2.52 (m, 2H), 1.89 (m, 4H), 1.78 (m, 2H).

$^{13}$C NMR (DMSO-d$_6$): 173.8, 164.4, 163.4, 152.9, 152.2, 149.2 (dd, J=246.5, 24.7), 149.0 (dd, J=246.5, 24.2), 148.9, 146.8, 138.0 (t, J=4.5), 136.7, 123.0 (dd, J=6.7, 3.5), 121.7, 121.3, 117.9 (d, J=17.2), 115.3 (d, J=17.6), 103.1, 71.8, 66.7, 58.2, 54.4, 52.3, 51.8, 51.7, 41.9, 38.1, 29.7, 24.9.

Type A is characterized by a differential scanning calorimetry (DSC) curve, at a heating rate of 10° C./min in an open cup under flowing nitrogen, exhibiting a relatively broad endotherm with an extrapolated onset temperature of about 56° C., a peak temperature of about 90° C. and an associated heat of about 23 J/gm followed by an endotherm with an extrapolated onset temperature of about 108° C., peak temperature of about 115° C. and an associated heat of about 13 J/gm followed by an endotherm with an extrapolated onset temperature of about 145° C., a peak temperature of about 148° C. and an associated heat of about 57 J/gm. The two low temperature endotherms are due to the loss of isopropanol and the high temperature endotherm is due to melting with decomposition of the remaining unsolvated phase (Type B).

The X-ray powder diffraction pattern of Type A is characterized by d-spacings of 14.91, 8.32, 6.88, 5.41, 4.74, 4.29, 4.04, 3.86, 3.75 and 3.59 Å.

A second crystalline form of (1), designated as Type B which is unsolvated material, was prepared either by swishing Type A in ethanol followed by filtration and subsequent drying, or by heating Type A to ~115° C. for about 20 minutes.

More specifically, Compound A tartrate salt Type A (2-propanol solvate) (10 g) was suspended in ethanol (50 mL) at 0° C. in a flask fitted with a mechanical stirrer, addition funnel, and thermocouple under a N$_2$ atmosphere. The solution was aged for 2 hours and then filtered. The cake was rinsed with ethanol (2×5 mL) and dried by pulling N$_2$ through the cake to afford Compound A tartrate salt Type B as a white, free-flowing solid. The $^1$H and $^{13}$C NMR spectra for Type B are identical to the spectra for Type A shown above.

Type B is characterized by a differential scanning calorimetry (DSC) curve, at a heating rate of 10° C./min in an open cup under flowing nitrogen, exhibiting an endotherm with an extrapolated onset temperature of about 144° C., a peak temperature of about 148° C. and an associated heat of about 65 J/gm. The endotherm is due to melting with decomposition.

The X-ray powder diffraction pattern of Type B is characterized by d-spacings of 13.29, 7.82, 6.63, 6.20, 5.36, 5.01, 4.59, 4.35, 4.05, 3.73 and 3.60 Å.

EXAMPLE 19

Resolution of Racemic Ester using Metarhizium anisopliae MF 6527

A frozen suspension of the fungus *Metarhizium anisopliae* MF 6527 (stored in 25% glycerol at −70° C.) was used to inoculate a 250 mL Erlenmeyer flask containing 50 mL of Sabouraud dextrose broth (Difco, Detroit Mich.). The flask was incubated at 29° C. with shaking for 72 hours. Four 2-L flasks, containing each 500 mL of Sabouraud dextrose were inoculated each with 10 mL of the first seed stage and were incubated at 29° C. for 48 hours with shaking. The contents of the four 2 L flasks were pooled and used to inoculate a fermentor containing 180 L of Sabouraud dextrose broth and 0.1% of antifoam P 2000 (Dow Chemical, Midland Mich.). The fermentor was operated at 29° C., with 100 rpm agitation. The culture was aerated by pumping air into the fermentor at a flow of 100 L per minute. The head space of the fermentor was maintained at 0.7 bar. The culture was allowed to grow for 20 hours. A volume of 25 L of culture was transferred from the seed fermentor and used to inoculate a production fermentor containing 600 L of Sabouraud dextrose medium supplemented with 2.5 g/l of casamino acids (Difco, Detroit Mich.) and 0.1% of antifoam P 2000. The production fermentor was operated at 29° C., with an agitation of 100 rpm. The culture was aerated by pumping air at a flow of 100 L per minute. The head space of the fermentor was maintained at 0.7 bar. The pH of the culture was maintained between 7.3 and 7.5 for the duration of the experiment. After 170 hours of incubation, the entire contents of the fermentor were pumped through a 0.2 uM membrane and the resulting filtrate was stored at 4° C. overnight. The filtrate was then washed by diafiltration against 2 volumes of 50 mM Tris buffer (pH 8.5), using a 10,000 dalton cut off membrane. The washed fermentation broth was concentrated 26 fold, employing the same filtration device and was stored at 4° C. The concentrate was further concentrated by 8.3 fold using a 6 square feet regenerated cellulose TFF cartridge (Millipore SK1PC003W4, Millipore, Bedford Mass.) with a 10,000 dalton cut off. Ammonium sulfate (166 g) was slowly added over 20 min to 1 L of the concentrate under stirring, to reach 30% saturation. The mixture was stirred for an additional 20 min and was centrifuged at 10,000 rpm for 35 min at 4° C. To the resulting supernatant was added 272 g of ammonium sulfate (over 20 min) under stirring to reach 70% saturation. The mixture was stirred for an additional 20 min and was centrifuged at 10,000 rpm for 35 min. The resulting pellet was stored at 4° C. An amount of 3.05 g of pellet was dissolved into 50 mL of Tris buffer (50 mM, pH 8.5). (±)-2-ester in DMSO (final concentration of 2%) was added to the resuspended pellet at a final concentration of 1 g/L. The reaction mixture was incubated at 29° C. with stirring. A (S)-DHP methyl ester (+)-S-2 enantiomeric excess greater than 98% was achieved after 10 days of incubation, as determined by the SFC assay described in Example 12.

While the foregoing specification teaches the principles of the present invention, with examples provided for the purpose of illustration, it will be understood that the practice of the invention encompasses all of the usual variations, adaptations, modifications, deletions or additions of procedures and protocols described herein, as come within the scope of the following claims and its equivalents.

What is claimed is:

1. A process for the preparation of a compound of Formula (I):

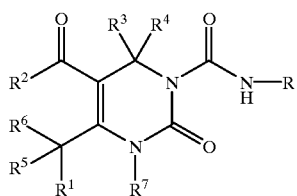

(I)

comprises treating a dihydropyrimidinone of Formula (II):

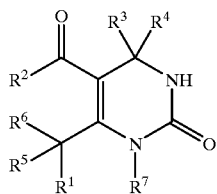

(II)

with a deprotonation agent; then contacting the treated dihydropyrimidinone with carbonyldiimidazole to form an acylimidazolide intermediate; and then contacting the acylimidazolide intermediate with an amine of Formula (III):

$H_2N-R$ (III)

to form the compound of Formula (I); wherein
$R^1$, $R^5$ and $R^6$ are each independently selected from:
1) hydrogen,
2) halogen,
3) $C_{1-10}$ alkyl,
4) $C_{3-8}$ cycloalkyl,
5) substituted $C_{1-10}$ alkyl, wherein the substituents are independently selected from halogen, $C_{1-6}$ alkoxy, halogen-substituted $C_{1-6}$ alkoxy, $C_{3-6}$ cycloalkyl, phenyl, and halogen-substituted phenyl,
6) substituted $C_{3-8}$ cycloalkyl, wherein the substituents are independently selected from halogen, $C_{1-6}$ alkoxy, halogen-substituted $C_{1-6}$ alkoxy, $C_{1-6}$ alkyl, halogen-substituted $C_{1-6}$ alkyl, phenyl, and halogen-substituted phenyl,
7) phenyl, and
8) substituted phenyl, wherein the substituents are independently selected from halogen, $C_{1-4}$ alkyl, halogen-substituted $C_{1-4}$ alkyl, cyano, nitro, and $C_{1-4}$ alkoxy; or $R^1$ is $C_1$–$C_4$ alkoxy and $R^5$ and $R^6$ are each as defined above; or $R^1$ is as defined above and $R^5$ and $R^6$ together form a 3- to 7-membered saturated or unsaturated carbocyclic ring or a 4- to 7-membered saturated or unsaturated heterocyclic ring, the carbocyclic ring or heterocyclic ring optionally substituted with $C_{1-6}$ alkyl, wherein the heterocylic ring contains from 1 to 3 heteroatoms independently selected from nitrogen, oxygen, and sulfur;

$R^2$ is:
1) hydrogen,
2) hydroxy,
3) $C_{1-10}$ alkyl,
4) halogen-substituted $C_{1-10}$ alkyl,
5) $C_{1-6}$ alkoxy,
6) halogen-substituted $C_{1-6}$ alkoxy,
7) $C_{3-6}$ cycloalkyl, or
8) substituted $C_{3-6}$ cycloalkyl, wherein the substituents are independently selected from halogen, hydroxy, $C_{1-6}$ alkyl, halogen-substituted $C_{1-6}$ alkyl, and $C_{1-6}$ alkoxy;

$R^3$ and $R^4$ are each independently selected from hydrogen, $C_{1-10}$ alkyl, and the group of Formula (IV):

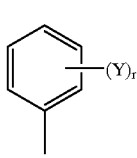

(IV)

wherein each Y is independently selected from
1) halogen,
2) cyano,
3) $C_{1-6}$ alkoxy,
4) nitro,
5) $C_{1-10}$ alkyl, and
6) halogen-substituted $C_{1-10}$ alkyl;

r is an integer of from 0 to 5;

$R^7$ is selected from hydrogen and $C_{1-10}$ alkyl; and

R is selected from $C_{1-40}$ hydrocarbyl and substituted $C_{1-40}$ hydrocarbyl.

2. The process according to claim 1, wherein R is selected from
1) $C_{1-16}$ alkyl,
2) substituted $C_{1-16}$ alkyl wherein the substituents are independently selected from halogen, hydroxy, $C_{3-8}$ cycloalkyl, $C_{1-4}$ alkoxy, cyano, nitro, NHR$^a$, and N(R$^a$)$_2$,
3) $C_{5-7}$ cycloalkyl,
4) substituted $C_{5-7}$ cycloalkyl, wherein the substituents are independently selected from halogen, hydroxy, $C_{1-10}$ alkyl, $C_{1-4}$ alkoxy, cyano, nitro, NHR$^a$, and N(R$^a$)$_2$,
5) phenyl,
6) substituted phenyl, wherein the substituents are independently selected from halogen, $C_{1-4}$ alkyl, halogen-substituted $C_{1-4}$ alkyl, cyano, nitro, and $C_{1-4}$ alkoxy, and 7) the group represented by Formula (V):

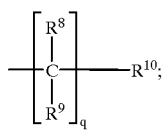

(V)

wherein $R^8$ and $R^9$ are independently selected from
1) hydrogen,
2) $C_{1-4}$ alkyl, and
3) $C_{5-7}$ cycloalkyl;
$R^{10}$ is independently selected from

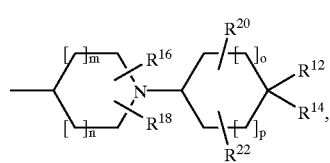

(VI)

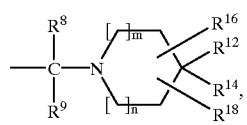

(VII)

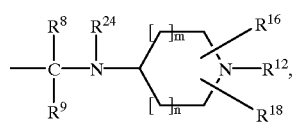

(VIII)

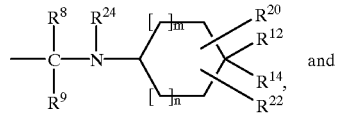

(IX) and

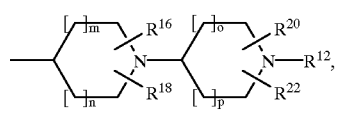

(X)

wherein $R^{12}$ is selected from
1) phenyl
2) substituted phenyl, wherein the substituents on the phenyl are independently selected from halogen, hydroxy, trifluoromethyl, cyano, nitro, $C_{1-4}$ alkyl, $C_{1-4}$ alkoxy, $NHR^a$, and $N(R^a)_2$, and
3) unsubstituted or substituted pyridyl, pyridyl N-oxide (N->O), pyrazinyl, thienyl, thiazolyl, furanyl, quinazolinyl, or naphthyl wherein the substituents thereon are independently selected from halogen, trifluoromethyl, cyano, nitro, $C_{1-4}$ alkyl, $C_{1-4}$ alkoxy, phenyl, $C_{3-8}$ cycloalkyl, $NHR^a$, and $N(R^a)_2$;
$R^{14}$ is selected from
1) hydrogen,
2) cyano,
3) $C_{1-4}$ alkyl,
4) $OR^b$,
5) $CO_2R^b$,
6) $CON(R^a)_2$,
7) phenyl,
8) substituted phenyl wherein the substituents on the phenyl are independently selected from halogen, trifluoromethyl, cyano, nitro, $C_{1-4}$ alkyl, $C_{1-4}$ alkoxy, $NHR^a$, and $N(R^a)_2$, and
9) unsubstituted or substituted pyridyl, thienyl, furanyl or naphthyl wherein the substituents thereon are independently selected from trifluoromethyl, phenyl, halogen, $C_{1-4}$ alkyl, $C_{1-4}$ alkoxy, and $C_{3-8}$ cycloalkyl;
$R^{16}$, $R^{18}$, $R^{20}$ and $R^{22}$ are each independently selected from hydrogen, $C_{1-10}$ alkyl, $C_{3-8}$ cycloalkyl, $(CH_2)_{0-4}OR^a$, $(CH_2)_{0-4}CF_3$, $(CH_2)_{0-4}CO_2R^a$, $(CH_2)_{0-4}CN$, $(CH_2)_{0-4}NHR^a$, and $(CH_2)_{0-4}N(R^a)_2$;
$R^{24}$ is selected from hydrogen, $C_{1-4}$ alkyl, and $C_{5-7}$ cycloalkyl;
$R^a$ is $C_{1-4}$ alkyl;
$R^b$ is hydrogen, $C_{1-4}$ alkyl, $C_{3-8}$ cycloalkyl, or $(CH_2)_{1-4}CF_3$;
m, n, o, and p are each independently selected from 0, 1, and 2, with the proviso that the sum of m+n and the sum of o+p are independently never greater than 3; and
q is an integer from 0 to 4.

3. The process according to claim 2, wherein
$R^1$, $R^5$ and $R^6$ are each independently selected from hydrogen, halogen, $C_{1-4}$ alkyl, and substituted $C_{1-4}$ alkyl, wherein the substituents are independently selected from halogen, $C_{1-4}$ alkoxy, and halogen-substituted $C_{1-4}$ alkoxy;
$R^2$ is hydrogen, $C_{1-4}$ alkyl, halogen-substituted $C_{1-4}$ alkyl, or $C_{1-4}$ alkoxy;
$R^3$ and $R^4$ are each independently selected from hydrogen, $C_{1-4}$ alkyl, and the group of Formula (IV):

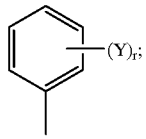

(IV)

$R^7$ is selected from hydrogen and $C_{1-4}$ alkyl;
R is selected from
1) $C_{3-12}$ alkyl,
2) substituted $C_{3-12}$ alkyl wherein the substituents are independently selected from halogen, hydroxy, $C_{1-4}$ alkoxy, cyano, and nitro,
3) $C_{5-7}$ cycloalkyl,
4) substituted $C_{5-7}$ cycloalkyl, wherein the substituents are independently selected from halogen, hydroxy, $C_{1-4}$ alkyl, $C_{1-4}$ alkoxy, cyano, and nitro,
5) substituted phenyl, wherein the substituents are independently selected from halogen, $C_{1-4}$ alkyl, halogen-substituted $C_{1-4}$ alkyl, cyano, nitro, and $C_{1-4}$ alkoxy, and 6) the group of Formula (V):

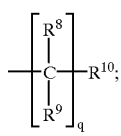
(V)

wherein $R^{10}$ is independently selected from the structure of Formula (VI) and the structure of Formula (VII);

$R^{12}$ is selected from phenyl; substituted phenyl, wherein the substituents on the phenyl are independently selected from halogen, trifluoromethyl, cyano, nitro, $C_{1-4}$ alkyl, and $C_{1-4}$ alkoxy; and unsubstituted or substituted pyridyl wherein the substituents on the pyridyl are independently selected from halogen, trifluoromethyl, cyano, nitro, $C_{1-4}$ alkyl, and $C_{1-4}$ alkoxy;

$R^{14}$ is selected from hydrogen; cyano; $C_{1-4}$ alkyl; $OR^b$; phenyl; substituted phenyl wherein the substituents on the phenyl are independently selected from halogen, trifluoromethyl, cyano, nitro, $C_{1-4}$ alkyl, and $C_{1-4}$ alkoxy; and unsubstituted or substituted pyridyl wherein the substituents on the pyridyl are independently selected from trifluoromethyl, phenyl, halogen, $C_{1-4}$ alkyl, and $C_{1-4}$ alkoxy;

$R^{16}$, $R^{18}$, $R^{20}$ and $R^{22}$ are each independently selected from hydrogen, $C_{1-4}$ alkyl, $(CH_2)_{0-4}OR^a$, $(CH_2)_{0-4}CF_3(CH_2)_{0-4}CO_2R^a$, and $(CH_2)_{0-4}CN$; and $R^{24}$ is selected from hydrogen and $C_{1-4}$ alkyl.

4. The process according to claim 2, wherein
$R^1$ is hydrogen, $C_{1-4}$ alkyl, or $C_{1-4}$ alkoxy;
$R^5$ and $R^6$ are each hydrogen;
$R^2$ is $C_{1-4}$ alkyl or $C_{1-4}$ alkoxy;
$R^3$ is selected from $C_{1-4}$ alkyl and the group of Formula (IV)
$R^4$ is hydrogen;
$R^7$ is selected from hydrogen and $C_{1-4}$ alkyl;
R is the group of Formula (V):

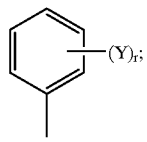
(V)

wherein either $R^8$ is hydrogen and $R^9$ is $C_{1-4}$ alkyl, or $R^8$ and $R^9$ are both hydrogen;

$R^{12}$ is selected from phenyl; substituted phenyl, wherein the substituents on the phenyl are independently selected from halogen, trifluoromethyl, cyano, nitro, $C_{1-4}$ alkyl, and $C_{1-4}$ alkoxy; and unsubstituted or substituted pyridyl wherein the substituents on the pyridyl are independently selected from halogen, trifluoromethyl, cyano, nitro, $C_{1-4}$ alkyl, and $C_{1-4}$ alkoxy;

$R^{14}$ is selected from hydrogen; cyano; $C_{1-4}$ alkyl; $OR^b$; phenyl; substituted phenyl wherein the substituents on the phenyl are independently selected from halogen, trifluoromethyl, cyano, nitro, $C_{1-4}$ alkyl, and $C_{1-4}$ alkoxy; and unsubstituted or substituted pyridyl wherein the substituents on the pyridyl are independently selected from trifluoromethyl, phenyl, halogen, $C_{1-4}$ alkyl, and $C_{1-4}$ alkoxy; and r is an integer from 0 to 3.

5. The process according to claim 2, wherein
$R^1$ is selected from halogen, $C_{1-4}$ alkyl, $(CH_2)_{0-4}CF_3$, and $C_{1-4}$ alkoxy;
$R^2$ is selected from $C_{1-4}$ alkyl, $(CH_2)_{1-4}CF_3$, $C_{1-4}$ alkoxy, and $O(CH_2)_{1-4}CF_3$;
$R^3$ is a group of Formula (IV):

(IV)

wherein each Y is independently selected from halogen, cyano, $CF_3$, nitro, $C_{1-4}$ alkyl, and $C_{1-4}$ alkoxy;

$R^4$, $R^5$, $R^6$, and $R^7$ are each hydrogen;
R is $(CH_2)_qR^{10}$ wherein $R^{10}$ is independently selected from:

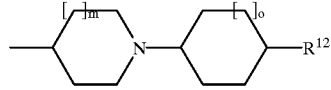
(XIV)

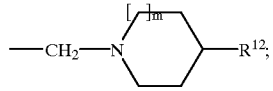
(XV)

wherein
$R^{12}$ is selected from phenyl; substituted phenyl, wherein the substituents on the phenyl are independently selected from halogen, trifluoromethyl, cyano, nitro, $C_{1-4}$ alkyl, and $C_{1-4}$ alkoxy; and unsubstituted or substituted pyridyl wherein the subsitituents on the pyridyl are independently selected from halogen, trifluoromethyl, cyano, nitro, $C_{1-4}$ alkyl, and $C_{1-4}$ alkoxy;

m and n are independently integers equal to 0 or 1;
q is an integer from 0 to 3; and
r is an integer from 0 to 3.

6. The process according to claim 5 for the preparation of (4S)-trans-4-(3,4-difluorophenyl)-3-[1-(4-pyridinyl-2-ylcyclohexyl)-(3R)-pyrrolidin-3-ylcarbamoyl]-6-methyl-2-oxo-1,2,3,4-tetrahydro-pyrimidine-5-carboxylic acid methyl ester of structural forrnula:

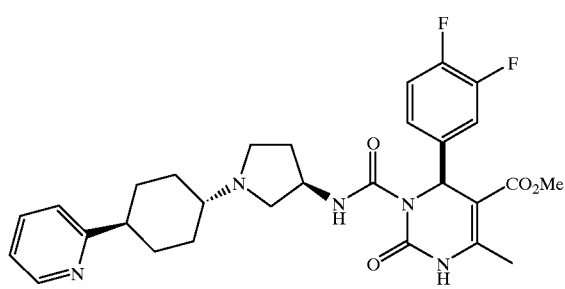

and Compound A, of structural formula:
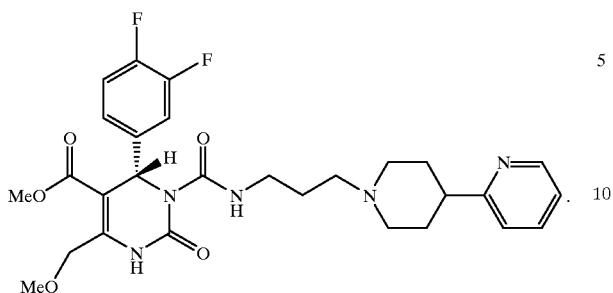
7. The process according to claim 1, wherein the deprotonation agent is selected from the group consisting of alkali metal carbonates and bicarbonates, alkali metal salts of di-$C_{1-4}$ alkylamines, alkali metal salts of $C_{1-6}$ hydrocarbons, and alkali metal salts of bis (tri-$C_{1-4}$ alkylsilyl)amines.
* * * * *